US011058901B2

(12) United States Patent
Soltani et al.

(10) Patent No.: US 11,058,901 B2
(45) Date of Patent: Jul. 13, 2021

(54) ULTRASOUND THERAPY SYSTEM

(71) Applicant: EKOS CORPORATION, Bothell, WA (US)

(72) Inventors: Azita Soltani, Snohomish, WA (US); Adrian F. Prokop, Seattle, WA (US)

(73) Assignee: EKOS CORPORATION, Bothell, WA (US)

( * ) Notice: Subject to any disclaimer, the term of this patent is extended or adjusted under 35 U.S.C. 154(b) by 193 days.

(21) Appl. No.: 16/268,075

(22) Filed: Feb. 5, 2019

(65) Prior Publication Data

US 2019/0269944 A1    Sep. 5, 2019

Related U.S. Application Data

(60) Continuation of application No. 13/176,613, filed on Jul. 5, 2011, now Pat. No. 10,232,196, which is a
(Continued)

(51) Int. Cl.
*A61B 6/00* (2006.01)
*A61N 7/02* (2006.01)
(Continued)

(52) U.S. Cl.
CPC .......... *A61N 7/022* (2013.01); *A61B 17/2202* (2013.01); *A61M 25/0032* (2013.01);
(Continued)

(58) Field of Classification Search
IPC ................................ A61B 17/22; A61N 7/022
See application file for complete search history.

(56) References Cited

U.S. PATENT DOCUMENTS 2,961,382 A    11/1960    Singher et al.
3,352,303 A    11/1967    Delaney
(Continued)

FOREIGN PATENT DOCUMENTS

AU    6334470    3/1989
EP    0 224 934    6/1987
(Continued)

OTHER PUBLICATIONS

Butler PhD, Bruce D., "Production of Microbubbles for Use as Echo Contrast Agents", Journal of Clinical Ultrasound, Jun. 1986, vol. 14, pp. 408-412.
(Continued)

*Primary Examiner* — Joel F Brutus
(74) *Attorney, Agent, or Firm* — Seager, Tufte & Wickhem, LLP

(57) ABSTRACT

In one embodiment of the present invention, a system for treating an occlusion within a patient's vasculature with ultrasonic energy comprises a catheter configured to be passed through the patient's vasculature such that a portion of the catheter is positioned at an intravascular treatment site. The system further comprises an ultrasound radiating member, an ultrasound signal generator configured to supply a drive signal to the ultrasound radiating member, an infusion pump configured to pump a therapeutic compound into the fluid delivery lumen so as to cause the therapeutic compound to be delivered to the treatment site and a controller configured to control the ultrasound signal generator and the infusion pump.

26 Claims, 26 Drawing Sheets

Related U.S. Application Data division of application No. 11/739,629, filed on Apr. 24, 2007, now abandoned.

(60) Provisional application No. 60/794,330, filed on Apr. 24, 2006, provisional application No. 60/799,119, filed on May 9, 2006.

(51) Int. Cl.
*A61B 17/22* (2006.01)
*A61M 25/00* (2006.01)
*A61M 37/00* (2006.01)

(52) U.S. Cl.
CPC ............... *A61M 37/0092* (2013.01); *A61B 2017/22088* (2013.01); *A61B 2017/22089* (2013.01); *A61M 25/003* (2013.01); *Y10T 29/49826* (2015.01)

(56) References Cited

U.S. PATENT DOCUMENTS

| | | |
|---|---|---|
| 3,430,625 A | 3/1969 | McLeod, Jr. |
| 3,565,062 A | 2/1971 | Kuris |
| 3,827,115 A | 8/1974 | Bom |
| 3,861,391 A | 1/1975 | Antonevich et al. |
| 3,941,122 A | 3/1976 | Jones |
| 4,192,294 A | 3/1980 | Vasilevsky et al. |
| 4,309,989 A | 1/1982 | Fahim |
| 4,319,580 A | 3/1982 | Colley et al. |
| 4,354,502 A | 10/1982 | Colley et al. |
| 4,466,442 A | 8/1984 | Hilmann et al. |
| 4,657,543 A | 4/1987 | Langer et al. |
| 4,657,756 A | 4/1987 | Rasor et al. |
| 4,682,596 A | 7/1987 | Bales et al. |
| 4,692,139 A | 9/1987 | Stiles |
| 4,750,902 A | 6/1988 | Wuchinich |
| 4,762,915 A | 8/1988 | Kung et al. |
| 4,772,594 A | 9/1988 | Hashimoto et al. |
| 4,774,958 A | 10/1988 | Feinstein |
| 4,797,285 A | 1/1989 | Barenholz et al. |
| 4,808,153 A | 2/1989 | Parisi |
| 4,821,740 A | 4/1989 | Tachibana et al. |
| 4,844,882 A | 7/1989 | Widder et al. |
| 4,870,953 A | 10/1989 | DonMicheal et al. |
| 4,900,540 A | 2/1990 | Ryan et al. |
| 4,920,954 A | 5/1990 | Alliger |
| 4,921,478 A | 5/1990 | Solano et al. |
| 4,936,281 A | 6/1990 | Stasz |
| 4,948,587 A | 8/1990 | Kost et al. |
| 4,953,565 A | 9/1990 | Tachibana et al. |
| 4,971,991 A | 11/1990 | Umemura et al. |
| 5,007,438 A | 4/1991 | Tachibana et al. |
| 5,040,537 A | 8/1991 | Katakura |
| 5,058,570 A | 10/1991 | Idemoto et al. |
| 5,069,664 A | 12/1991 | Guess |
| 5,076,276 A | 12/1991 | Sakurai et al. |
| 5,088,499 A | 2/1992 | Unger |
| 5,129,883 A | 7/1992 | Black |
| 5,149,319 A | 9/1992 | Unger |
| 5,156,050 A | 10/1992 | Schmid et al. |
| 5,158,071 A | 10/1992 | Umemura et al. |
| 5,163,421 A | 11/1992 | Bernstein et al. |
| 5,163,436 A | 11/1992 | Saitoh et al. |
| 5,197,946 A | 3/1993 | Tachibana |
| 5,209,720 A | 5/1993 | Unger |
| 5,215,680 A | 6/1993 | D'Arrigo |
| 5,216,130 A | 6/1993 | Line et al. |
| 5,261,291 A | 11/1993 | Schoch et al. |
| 5,267,954 A | 12/1993 | Nita |
| 5,269,291 A | 12/1993 | Carter |
| 5,277,913 A | 1/1994 | Thompson et al. |
| 5,279,546 A | 1/1994 | Mische et al. |
| 5,289,831 A | 3/1994 | Bosley |
| 5,304,115 A | 4/1994 | Pflueger |
| 5,307,816 A | 5/1994 | Hashimoto |
| 5,315,998 A | 5/1994 | Tachibana et al. |
| 5,318,014 A | 6/1994 | Carter |
| 5,326,342 A | 7/1994 | Pflueger |
| 5,342,292 A | 8/1994 | Nita et al. |
| 5,342,608 A | 8/1994 | Moriya et al. |
| 5,344,395 A | 9/1994 | Whalen et al. |
| 5,345,940 A | 9/1994 | Seward |
| 5,362,309 A | 11/1994 | Carter |
| 5,368,036 A | 11/1994 | Tanaka et al. |
| 5,368,557 A | 11/1994 | Nita |
| 5,368,558 A | 11/1994 | Nita |
| 5,380,273 A | 1/1995 | Dubrul et al. |
| 5,401,237 A | 3/1995 | Tachibana et al. |
| 5,423,797 A | 6/1995 | Adrian et al. |
| 5,431,663 A | 7/1995 | Carter |
| 5,440,914 A | 8/1995 | Tachibana et al. |
| 5,447,509 A | 9/1995 | Mills et al. |
| 5,456,259 A | 10/1995 | Barlow et al. |
| 5,474,530 A | 12/1995 | Passafaro |
| 5,474,531 A | 12/1995 | Carter |
| 5,498,236 A | 3/1996 | Dubrul et al. |
| 5,509,896 A | 4/1996 | Carter |
| 5,542,917 A | 8/1996 | Nita et al. |
| 5,542,935 A | 8/1996 | Unger et al. |
| 5,558,092 A | 9/1996 | Unger et al. |
| 5,580,575 A | 12/1996 | Unger et al. |
| 5,582,586 A | 12/1996 | Tachibana et al. |
| 5,585,112 A | 12/1996 | Unger et al. |
| 5,603,327 A | 2/1997 | Eberle |
| 5,606,974 A | 3/1997 | Castellano |
| 5,620,409 A | 4/1997 | Gans et al. |
| 5,624,382 A | 4/1997 | Oppelt |
| 5,628,728 A | 5/1997 | Tachibana et al. |
| 5,630,837 A | 5/1997 | Crowley |
| 5,648,098 A | 7/1997 | Porter |
| 5,660,909 A | 8/1997 | Tachibana et al. |
| 5,681,296 A | 10/1997 | Ishida |
| 5,695,460 A | 12/1997 | Siegel et al. |
| 5,707,608 A | 1/1998 | Liu |
| 5,713,848 A | 2/1998 | Dubrul et al. |
| 5,718,921 A | 2/1998 | Mathiowitz et al. |
| 5,720,710 A | 2/1998 | Tachibana et al. |
| 5,724,976 A | 3/1998 | Hirama et al. |
| 5,725,494 A | 3/1998 | Brisken |
| 5,728,062 A | 3/1998 | Brisken |
| 5,733,572 A | 3/1998 | Unger et al. |
| 5,735,811 A | 4/1998 | Brisken |
| 5,752,930 A | 5/1998 | Baudino et al. |
| 5,776,429 A | 7/1998 | Unger et al. |
| 5,817,048 A | 10/1998 | Lawandy |
| 5,823,962 A | 10/1998 | Lerch et al. |
| 5,827,203 A | 10/1998 | Nita |
| 5,834,880 A | 11/1998 | Lewandowski et al. |
| 5,836,896 A | 11/1998 | Rosenschein |
| 5,840,031 A | 11/1998 | Crowley |
| 5,846,218 A | 12/1998 | Brisken et al. |
| 5,846,517 A | 12/1998 | Unger |
| 5,876,345 A | 3/1999 | Eaton et al. |
| 5,916,192 A | 6/1999 | Nita et al. |
| 5,925,016 A | 7/1999 | Chornenky et al. |
| 5,928,186 A | 7/1999 | Homsma et al. |
| 5,934,284 A | 8/1999 | Plaia et al. |
| 5,957,851 A | 9/1999 | Hossack |
| 5,957,882 A | 9/1999 | Nita et al. |
| 5,971,949 A | 10/1999 | Levin et al. |
| 5,976,120 A | 11/1999 | Chow et al. |
| 5,997,497 A | 12/1999 | Nita et al. |
| 6,001,069 A | 12/1999 | Tachibana et al. |
| 6,007,514 A | 12/1999 | Nita |
| 6,024,718 A | 2/2000 | Chen et al. |
| 6,063,069 A | 5/2000 | Cragg et al. |
| 6,066,123 A | 5/2000 | Bednarski et al. |
| 6,068,857 A | 5/2000 | Weitschies et al. |
| 6,088,613 A | 7/2000 | Unger |
| 6,089,573 A | 7/2000 | Udagawa |
| 6,096,000 A | 8/2000 | Tachibana et al. |
| 6,096,070 A | 8/2000 | Ragheb et al. |
| 6,113,558 A | 9/2000 | Rosenschein et al. |

(56) References Cited

U.S. PATENT DOCUMENTS

| | | | |
|---|---|---|---|
| 6,113,570 A | 9/2000 | Siegel et al. | |
| 6,117,101 A | 9/2000 | Diederich et al. | |
| RE36,939 E | 10/2000 | Tachibana et al. | |
| 6,135,976 A * | 10/2000 | Tachibana | A61K 41/0028 |
| | | | 604/101.03 |
| 6,149,596 A | 11/2000 | Bancroft | |
| 6,176,842 B1 | 1/2001 | Tachibana et al. | |
| 6,206,831 B1 | 3/2001 | Suorsa et al. | |
| 6,210,356 B1 | 4/2001 | Anderson et al. | |
| 6,210,393 B1 | 4/2001 | Brisken | |
| 6,221,038 B1 | 4/2001 | Brisken | |
| 6,228,046 B1 | 5/2001 | Brisken | |
| 6,235,024 B1 | 5/2001 | Tu | |
| 6,238,347 B1 | 5/2001 | Nix et al. | |
| 6,270,460 B1 | 8/2001 | McCartan et al. | |
| 6,277,077 B1 | 8/2001 | Brisken et al. | |
| 6,287,271 B1 | 9/2001 | Dubrul et al. | |
| 6,296,619 B1 | 10/2001 | Brisken et al. | |
| 6,312,402 B1 | 11/2001 | Hansmann | |
| 6,361,554 B1 | 3/2002 | Brisken | |
| 6,391,042 B1 | 5/2002 | Cimino | |
| 6,394,956 B1 | 5/2002 | Chandrasekaran et al. | |
| 6,398,772 B1 | 6/2002 | Bond et al. | |
| 6,398,792 B1 | 6/2002 | O'Connor | |
| 6,416,740 B1 | 7/2002 | Unger | |
| 6,454,737 B1 | 9/2002 | Nita et al. | |
| 6,454,757 B1 | 9/2002 | Nita et al. | |
| 6,458,118 B1 * | 10/2002 | Lent | A61M 5/14276 |
| | | | 604/288.01 |
| 6,464,680 B1 | 10/2002 | Brisken et al. | |
| 6,471,683 B2 | 10/2002 | Drasier et al. | |
| 6,478,765 B2 | 11/2002 | Siegel et al. | |
| 6,494,891 B1 | 12/2002 | Cornish et al. | |
| 6,506,584 B1 | 1/2003 | Chandler et al. | |
| 6,508,816 B2 | 1/2003 | Shadduck | |
| 6,524,251 B2 | 2/2003 | Rabiner et al. | |
| 6,524,271 B2 | 2/2003 | Brisken et al. | |
| 6,548,047 B1 | 4/2003 | Unger | |
| 6,551,337 B1 | 4/2003 | Rabiner et al. | |
| 6,558,366 B1 | 5/2003 | Drasler et al. | |
| 6,562,021 B1 | 5/2003 | Derbin et al. | |
| 6,565,552 B1 | 5/2003 | Barbut | |
| 6,575,956 B1 | 6/2003 | Brisken et al. | |
| 6,579,277 B1 | 6/2003 | Rabiner et al. | |
| 6,582,392 B1 | 6/2003 | Bennett et al. | |
| 6,585,678 B1 | 7/2003 | Tachibana et al. | |
| 6,589,253 B1 | 7/2003 | Cornish et al. | |
| 6,605,084 B2 | 8/2003 | Acker et al. | |
| 6,623,444 B2 | 9/2003 | Babaev | |
| 6,635,046 B1 | 10/2003 | Barbut | |
| 6,645,150 B2 | 11/2003 | Angelsen et al. | |
| 6,647,755 B2 | 11/2003 | Rabiner et al. | |
| 6,652,547 B2 | 11/2003 | Rabiner et al. | |
| 6,660,013 B2 | 12/2003 | Rabiner et al. | |
| 6,663,613 B2 | 12/2003 | Evans et al. | |
| 6,676,626 B1 | 1/2004 | Bennett et al. | |
| 6,682,502 B2 | 1/2004 | Bond et al. | |
| 6,689,086 B1 | 2/2004 | Nita et al. | |
| 6,695,781 B2 | 2/2004 | Rabiner et al. | |
| 6,695,782 B2 | 2/2004 | Ranucci et al. | |
| 6,695,785 B2 | 2/2004 | Brisken et al. | |
| 6,723,063 B1 | 4/2004 | Zhang et al. | |
| 6,723,064 B2 | 4/2004 | Babaev | |
| 6,726,698 B2 | 4/2004 | Cimino | |
| 6,730,048 B1 | 5/2004 | Hare et al. | |
| 6,733,451 B2 | 5/2004 | Rabiner et al. | |
| 6,740,040 B1 | 5/2004 | Mandrusov et al. | |
| 6,767,345 B2 | 6/2004 | St. Germain et al. | |
| 6,824,575 B1 | 11/2004 | Otomo et al. | |
| 6,830,577 B2 | 12/2004 | Nash et al. | |
| 6,849,062 B2 | 2/2005 | Kantor | |
| 6,855,123 B2 | 2/2005 | Nita | |
| 6,866,670 B2 | 3/2005 | Rabiner et al. | |
| 6,896,659 B2 | 5/2005 | Conston et al. | |
| 6,905,505 B2 | 6/2005 | Dodson, Jr. et al. | |
| 6,921,371 B2 | 7/2005 | Wilson | |
| 6,929,633 B2 | 8/2005 | Evans et al. | |
| 6,942,620 B2 | 9/2005 | Nita et al. | |
| 6,942,677 B2 | 9/2005 | Nita et al. | |
| 6,945,937 B2 | 9/2005 | Culp et al. | |
| 6,958,040 B2 | 10/2005 | Oliver | |
| 6,979,293 B2 | 12/2005 | Hansmann et al. | |
| 6,985,771 B2 | 1/2006 | Fischell et al. | |
| 7,137,963 B2 | 11/2006 | Nita et al. | |
| 7,141,044 B2 | 11/2006 | Gentsler | |
| 7,166,098 B1 | 1/2007 | Steward et al. | |
| 7,186,246 B2 | 3/2007 | Bennett et al. | |
| 7,220,233 B2 | 5/2007 | Nita et al. | |
| 7,220,239 B2 | 5/2007 | Wilson et al. | |
| 7,309,334 B2 | 12/2007 | von Hoffmann | |
| 7,335,180 B2 | 2/2008 | Nita et al. | |
| 7,341,569 B2 | 3/2008 | Soltani et al. | |
| 7,384,407 B2 | 6/2008 | Rodriguez et al. | |
| 7,503,895 B2 | 3/2009 | Rabiner et al. | |
| 7,540,852 B2 | 6/2009 | Nita et al. | |
| 7,567,016 B2 | 7/2009 | Lu et al. | |
| 7,604,608 B2 | 10/2009 | Nita et al. | |
| 7,621,902 B2 | 11/2009 | Nita et al. | |
| 7,621,929 B2 | 11/2009 | Nita et al. | |
| 7,648,478 B2 | 1/2010 | Soltani et al. | |
| 7,727,178 B2 | 6/2010 | Wilson | |
| 7,758,509 B2 | 7/2010 | Angelsen et al. | |
| 7,771,372 B2 | 8/2010 | Wilson | |
| 7,774,933 B2 | 8/2010 | Wilson et al. | |
| 7,789,830 B2 | 9/2010 | Fujita et al. | |
| 7,818,854 B2 | 10/2010 | Wilson | |
| 7,828,754 B2 | 11/2010 | Abe et al. | |
| 7,828,762 B2 | 11/2010 | Wilson | |
| 7,901,359 B2 | 3/2011 | Mandrusov et al. | |
| 7,914,509 B2 | 3/2011 | Bennett et al. | |
| 8,012,092 B2 | 9/2011 | Powers et al. | |
| 8,062,566 B2 | 11/2011 | Nita et al. | |
| 8,123,789 B2 | 2/2012 | Khanna | |
| 8,152,753 B2 | 4/2012 | Nita et al. | |
| 8,167,831 B2 | 5/2012 | Wilson | |
| 8,192,363 B2 | 6/2012 | Soltani et al. | |
| 8,696,612 B2 | 4/2014 | Wilson et al. | |
| 8,740,835 B2 | 6/2014 | Soltani et al. | |
| 9,192,566 B2 | 11/2015 | Soltani et al. | |
| 10,182,833 B2 | 1/2019 | Soltani et al. | |
| 10,188,410 B2 | 1/2019 | Soltani et al. | |
| 10,232,196 B2 | 3/2019 | Soltani et al. | |
| 2001/0003790 A1 | 6/2001 | Ben-Haim et al. | |
| 2001/0053384 A1 | 12/2001 | Greenleaf et al. | |
| 2002/0032394 A1 | 3/2002 | Brisken et al. | |
| 2002/0041898 A1 | 4/2002 | Unger et al. | |
| 2002/0045890 A1 | 4/2002 | Celliers et al. | |
| 2002/0052620 A1 | 5/2002 | Barbut | |
| 2002/0068869 A1 | 6/2002 | Brisken et al. | |
| 2002/0077550 A1 | 6/2002 | Rabiner et al. | |
| 2002/0082238 A1 | 6/2002 | Newman et al. | |
| 2002/0123787 A1 | 9/2002 | Weiss | |
| 2002/0151792 A1 | 10/2002 | Conston et al. | |
| 2002/0193708 A1 | 12/2002 | Thompson et al. | |
| 2003/0036705 A1 | 2/2003 | Hare et al. | |
| 2003/0040501 A1 | 2/2003 | Newman et al. | |
| 2003/0050662 A1 | 3/2003 | Don Michael | |
| 2003/0065263 A1 | 4/2003 | Hare et al. | |
| 2003/0069525 A1 | 4/2003 | Brisken et al. | |
| 2003/0083608 A1 | 5/2003 | Evans et al. | |
| 2003/0114869 A1 * | 6/2003 | Nash | A61B 17/320758 |
| | | | 606/159 |
| 2003/0139774 A1 | 7/2003 | Epstein et al. | |
| 2003/0163147 A1 | 8/2003 | Hare et al. | |
| 2003/0191446 A1 | 10/2003 | Tachibana et al. | |
| 2003/0236539 A1 | 12/2003 | Rabiner et al. | |
| 2004/0001809 A1 | 1/2004 | Brisken et al. | |
| 2004/0010290 A1 * | 1/2004 | Schroeppel | A61K 47/6957 |
| | | | 607/3 |
| 2004/0019318 A1 * | 1/2004 | Wilson | A61M 37/0092 |
| | | | 604/22 |
| 2004/0024347 A1 | 2/2004 | Wilson et al. | |
| 2004/0039311 A1 | 2/2004 | Nita et al. | |
| 2004/0049148 A1 | 3/2004 | Rodriguez et al. | |

(56) References Cited

U.S. PATENT DOCUMENTS

| | | |
|---|---|---|
| 2004/0054351 A1 | 3/2004 | Deniega et al. |
| 2004/0059313 A1 | 3/2004 | Anderson et al. |
| 2004/0068189 A1 | 4/2004 | Wilson et al. |
| 2004/0077976 A1 | 4/2004 | Wilson |
| 2004/0097996 A1 | 5/2004 | Hare et al. |
| 2004/0138570 A1 | 7/2004 | Nita et al. |
| 2004/0162571 A1 | 8/2004 | Rabiner et al. |
| 2004/0171981 A1 | 9/2004 | Buffen et al. |
| 2004/0220514 A1 | 11/2004 | Cafferata |
| 2004/0220544 A1* | 11/2004 | Heruth ............. A61M 5/14276 604/508 |
| 2004/0225318 A1* | 11/2004 | Eidenschink ....... A61M 25/104 606/194 |
| 2004/0236350 A1 | 11/2004 | Bolduc et al. |
| 2004/0255957 A1 | 12/2004 | Cafferata |
| 2004/0265393 A1 | 12/2004 | Unger et al. |
| 2005/0021063 A1 | 1/2005 | Hall et al. |
| 2005/0043629 A1 | 2/2005 | Rabiner et al. |
| 2005/0043753 A1 | 2/2005 | Rabiner et al. |
| 2005/0090818 A1 | 4/2005 | Pike, Jr. et al. |
| 2005/0096669 A1 | 5/2005 | Rabiner et al. |
| 2005/0113688 A1 | 5/2005 | Nita et al. |
| 2005/0119679 A1 | 6/2005 | Rabiner et al. |
| 2005/0124877 A1 | 6/2005 | Nita et al. |
| 2005/0137520 A1 | 6/2005 | Rule et al. |
| 2005/0187513 A1 | 8/2005 | Rabiner et al. |
| 2005/0187514 A1 | 8/2005 | Rabiner et al. |
| 2005/0197619 A1 | 9/2005 | Rule et al. |
| 2005/0209578 A1 | 9/2005 | Christian Evans et al. |
| 2005/0215942 A1 | 9/2005 | Abrahamson et al. |
| 2005/0215946 A1 | 9/2005 | Hansmann et al. |
| 2005/0216044 A1 | 9/2005 | Hong |
| 2005/0256410 A1 | 11/2005 | Rabiner et al. |
| 2006/0069303 A1 | 3/2006 | Couvillon |
| 2006/0106308 A1 | 5/2006 | Hansmann et al. |
| 2006/0173387 A1 | 8/2006 | Hansmann et al. |
| 2006/0184070 A1 | 8/2006 | Hansmann et al. |
| 2006/0264809 A1 | 11/2006 | Hansmann et al. |
| 2007/0037119 A1 | 2/2007 | Pal et al. |
| 2007/0038158 A1 | 2/2007 | Nita et al. |
| 2007/0066978 A1 | 3/2007 | Schafer et al. |
| 2007/0083120 A1 | 4/2007 | Cain et al. |
| 2007/0005051 A1 | 6/2007 | Kampa |
| 2007/0207194 A1* | 9/2007 | Grayburn ................ A61K 9/127 424/450 |
| 2007/0225619 A1 | 9/2007 | Rabiner et al. |
| 2007/0239027 A1 | 10/2007 | Nita |
| 2007/0265560 A1 | 11/2007 | Soltani et al. |
| 2008/0045865 A1 | 2/2008 | Kislev |
| 2008/0065014 A1 | 3/2008 | McCrystle et al. |
| 2008/0146918 A1 | 6/2008 | Magnin et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Matsunaga et al. |
| 2008/0221506 A1 | 9/2008 | Rodriguez et al. |
| 2008/0262350 A1 | 10/2008 | Unger |
| 2008/0306499 A1 | 12/2008 | Katoh et al. |
| 2008/0319355 A1 | 12/2008 | Nita |
| 2008/0319376 A1 | 12/2008 | Wilcox et al. |
| 2009/0018472 A1 | 1/2009 | Soltani et al. |
| 2009/0112150 A1 | 4/2009 | Unger et al. |
| 2009/0209900 A1 | 8/2009 | Carmeli et al. |
| 2009/0216246 A1 | 8/2009 | Nita et al. |
| 2010/0010393 A1 | 1/2010 | Duffy et al. |
| 2010/0022920 A1 | 1/2010 | Nita et al. |
| 2010/0022944 A1 | 1/2010 | Wilcox |
| 2010/0023036 A1 | 1/2010 | Nita et al. |
| 2010/0023037 A1 | 1/2010 | Nita et al. |
| 2010/0049209 A1 | 2/2010 | Nita et al. |
| 2010/0063413 A1 | 3/2010 | Volz |
| 2010/0063414 A1 | 3/2010 | Volz |
| 2010/0081934 A1 | 4/2010 | Hansmann et al. |
| 2010/0204582 A1 | 8/2010 | Lu |
| 2010/0210940 A1 | 8/2010 | Bradley et al. |
| 2010/0222715 A1 | 9/2010 | Nita |
| 2010/0256616 A1 | 10/2010 | Katoh et al. |
| 2010/0262215 A1 | 10/2010 | Gertner |
| 2010/0292685 A1 | 11/2010 | Katoh et al. |
| 2011/0160621 A1 | 6/2011 | Nita |
| 2011/0288449 A1 | 11/2011 | Schenkengel |
| 2011/0300078 A1 | 12/2011 | Borden et al. |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0059285 A1 | 3/2012 | Soltani et al. |
| 2012/0078140 A1 | 3/2012 | Nita |
| 2012/0123273 A1 | 5/2012 | Okuno et al. |
| 2012/0179073 A1 | 7/2012 | Nita |
| 2012/0197277 A1 | 8/2012 | Stinis |
| 2013/0204166 A1 | 8/2013 | Villanueva et al. |
| 2013/0216593 A1 | 8/2013 | Borden et al. |
| 2013/0289398 A1 | 10/2013 | Borden et al. |
| 2013/0331738 A1 | 12/2013 | Borrelli |
| 2014/0236005 A1 | 8/2014 | Chen et al. |

FOREIGN PATENT DOCUMENTS

| | | |
|---|---|---|
| EP | 0 278 074 | 8/1988 |
| EP | 0 327 490 | 8/1989 |
| EP | 0 744 189 | 11/1996 |
| EP | 1 090 658 | 4/2001 |
| EP | 1 252 885 | 10/2002 |
| GB | 1 577 551 | 10/1980 |
| JP | 52-115591 | 9/1977 |
| JP | 02-180275 | 7/1990 |
| WO | WO 80/001365 | 7/1980 |
| WO | WO 80/002365 | 11/1980 |
| WO | WO 89/005159 | 6/1989 |
| WO | WO 89/005160 | 6/1989 |
| WO | WO 89/006978 | 8/1989 |
| WO | WO 90/001971 | 3/1990 |
| WO | WO 95/015118 | 6/1995 |
| WO | WO 96/015815 | 5/1996 |
| WO | WO 96/027341 | 9/1996 |
| WO | WO 96/029935 | 10/1996 |
| WO | WO 96/036286 | 11/1996 |
| WO | WO 99/033500 | 7/1999 |
| WO | WO 99/039647 | 8/1999 |
| WO | WO 99/039738 | 8/1999 |
| WO | WO 00/038580 | 7/2000 |
| WO | WO 02/013678 | 2/2002 |
| WO | WO 02/015803 | 2/2002 |
| WO | WO 02/015804 | 2/2002 |
| WO | WO 03/051208 | 6/2003 |
| WO | WO 2005/027756 | 3/2005 |
| WO | WO 2005/084552 | 9/2005 |
| WO | WO 2005/084553 | 9/2005 |
| WO | WO 2007/127176 | 11/2007 |

OTHER PUBLICATIONS

Bao et al. "Transfection of a Reporter Plasmid into Cultured Cells by Sonoporation In Vitro," Ultrasound in Medicine and Biology Journal, 1997, vol. 23, No. 6, pp. 953-959.

Bleeker et al., "On the Application of Ultrasonic Contrast Agents for Blood Flowmetry and Assessment of Cardiac Perfusion", Journal of Ultrasound in Medicine, Aug. 1990, vol. 9, No. 8, pp. 461-471.

Chamsuddin et al., "Catheter-directed Thrombolysis with the Endowave System in the Treatment of Acute Massive Pulmonary Embolism: A Retrospective Multicenter Case Series," Journal of Vascular and Interventional Radiology, Mar. 2008, vol. 19, No. 3, pp. 372-376.

Feinstein et al., "Two-dimensional Contrast Echocardiography. I. In Vitro Development and Quantitative Analysis of Echo Contrast Agents", Journal of the American College of Cardiology, Jan. 1984, vol. 3, No. 1, pp. 14-20.

Greenleaf, William J. et al.; Artifical Cavitation Nuclei Significantly Enhance Acoustically Induced Cell Transfection. vol. 24, No. 4 pp. 587-595, 1998.

(56) References Cited

OTHER PUBLICATIONS

Holland et al., "Thresholds for Transient Cavitation Produced by Pulsed Ultrasound in a Controlled Nuclei Environment", The Journal of the Acoustical Society of America, Nov. 1990, vol. 88, No. 5, pp. 2059-2069.

International Search Report and Written Opinion in Application No. PCT/US2007/009867, dated Sep. 30, 2008.

Jeffers, R.J. et al.; Evaluation of the Effect of Cavitation Activity on Drug-Ultrasound Synergisms, 1993.

Jeffers, Russel et al.; Dimethylformamide as an Enhancer of Cavitation-Induced Cell Lysis In Vitro, vol. 97, No. 1, Jan. 1995.

Keller et al., "Automated Production and Analysis of Echo Contrast Agents", Journal of Ultrasound in Medicine, Sep. 1986, vol. 5, pp. 493-498.

Kim, Timothy F., "Microbubbles Show Promise for Enhancing Ultrasound Signal, Image, Other Applications", The Journal of the American Medical Association, Mar. 1989, vol. 281, No. 11, p. 1542.

Lang et al., "Contrast Ultrasonography of the Kidney: a New Method for Evaluation of Renal Perfusion in Vivo", Circulation, 1987, vol. 75, No. 1, pp. 229-234.

Leong et al., "Polyanhydrides for Controlled Release of Bioactive Agents", Biomaterials, Sep. 1986, vol. 7, pp. 364-371.

Lin et al., "Comparison of Percutaneous Ultrasound-Accelerated Thrombolysis versus Catheter-Directed Thrombolysis in Patients with Acute Massive Pulmonary Embolism," Vascular, 2009, vol. 17, No. 3, pp. S137-S147.

Meltzer et al., "The Source of Ultrasound Contrast Effect", Journal of Clinical Ultrasound, Apr. 1980, vol. 8, No. 2, pp. 121-127.

Miller, Douglas L. et al.; Sonoporation of Cultured Cells in the Rotation Tube Exposure System, vol. 25, No. 1, 1999.

Porter, T.R. et al., Thrombolytic Enhancement With Perfluorocarbom-Exposed Sonicated Dextrose Albumin Microbubbles, Nov. 1996.

Prat et al., "In Vivo Effects of Cavitation Alone or in Combination with Chemotherapy in a Peritoneal Carcinomatosis in the Rat," 1993, vol. 68, pp. 13-17.

Price et al.; Delivery of Colloidal Particles and Red Blood Cells to Tissue Through Microvessel Ruptures Created by Targeted Microbubble Destruction With Ultrasound, Sep. 29, 1998.

Saletes et al., "Cavitation par Excitation Acoustique Bifréquentielle: Application á la Thrombolyse Ultrsonore," N° d'ordre 311, Universite de Lyon, Dec. 7, 2009, pp. 110.

Tachibana K.; Albumin Microbubble Echo-Contrast Materials as an Enhancer for Ultrasound Accelerated Thrombolysis, Sep. 1, 1995.

Unger et al., "Ultrasound Enhances Gene Expression of Liposomal Transfection," Investigative Radiology, vol. 32, No. 12, pp. 723-727, 1997.

Unger et al., "Acoustically Active Liposheres Containing Paclitaxel," vol. 11, No. 12, 1992.

Vandenburg et al., "Myocardial Risk Area and Peak Gray Level Measurement by Contrast Echocardiography: Effect of Microbubble Size and Concentration, Injection Rate, and Coronary Vasodilation," American Heart Journal, Apr. 1988, vol. 115, No. 4, pp. 733-739.

Wheatly et al., "Contrast Agents for Diagnostic Ultrasound: Development and Evaluation of Polymer-Coated Microbubbles," Biomaterials, Nov. 1990, vol. 11, No. 19, pp. 713-717.

Wu, Yunqiu et al., "Binding as Lysing of Blood Clots Using MRX-408," Investigative Radiology, Dec. 1998, vol. 33, No. 12, pp. 880-885.

* cited by examiner

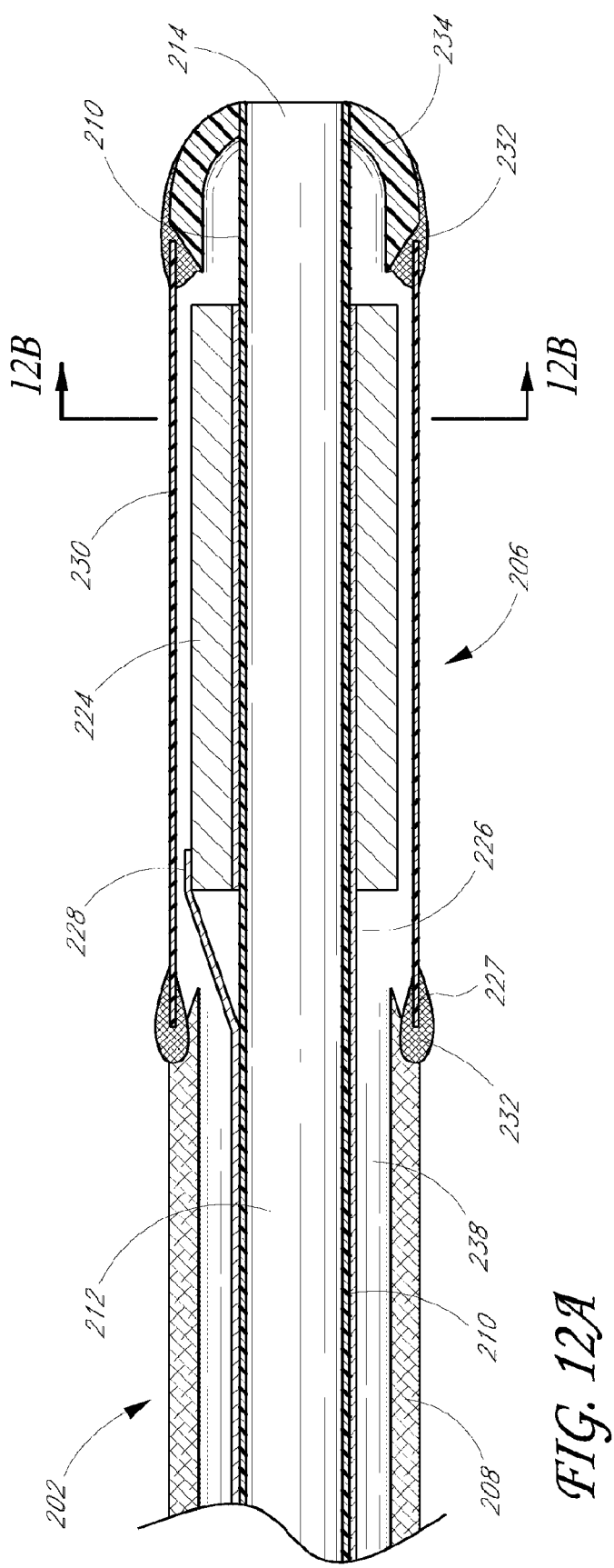
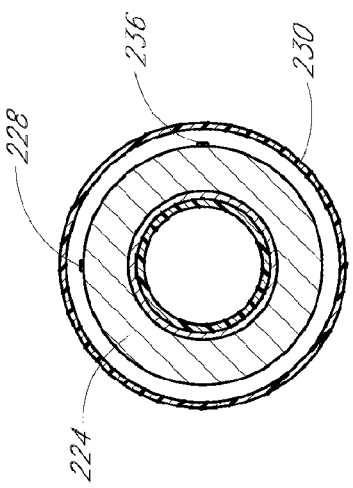
FIG. 12A
FIG. 12B

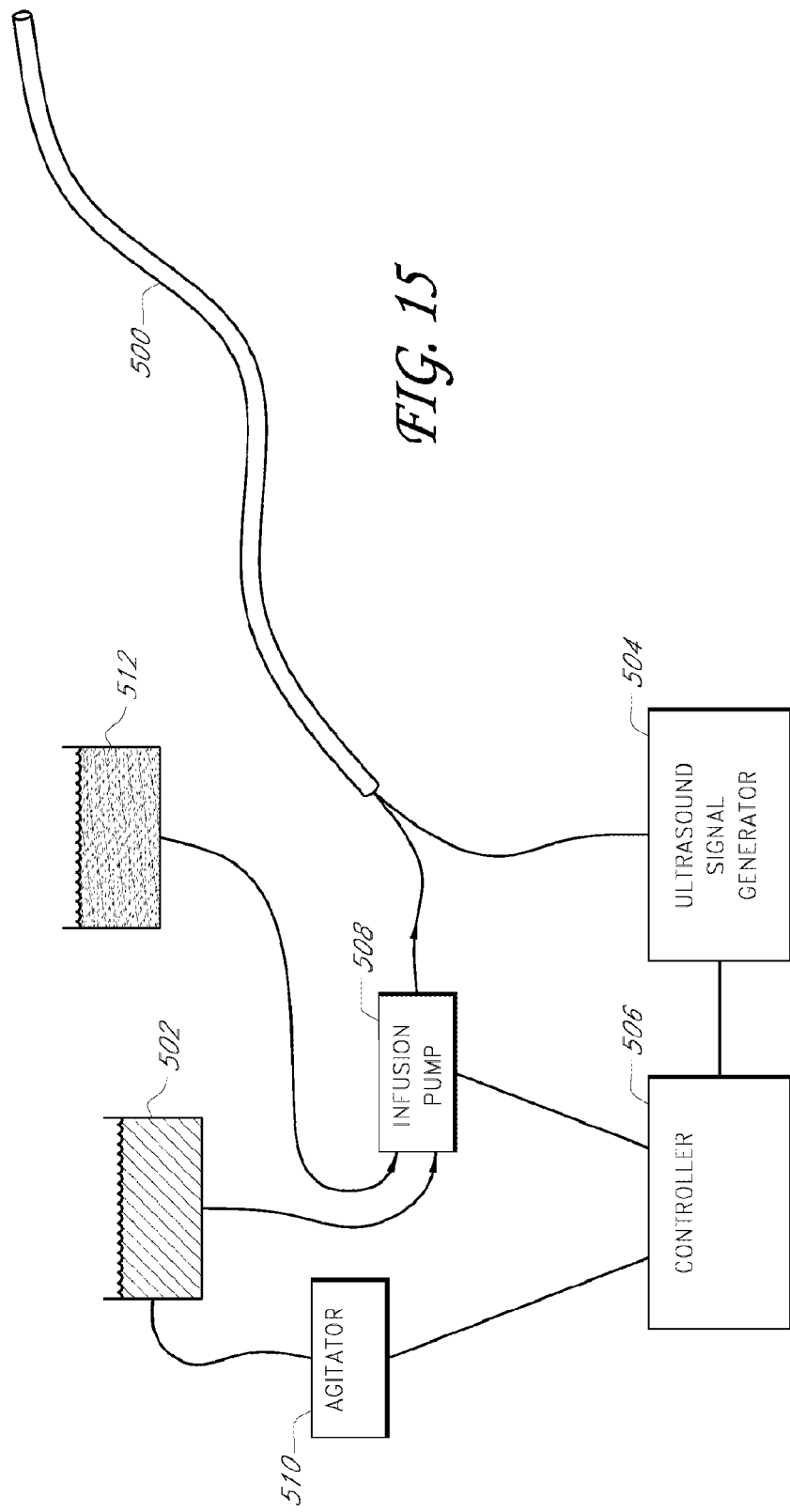

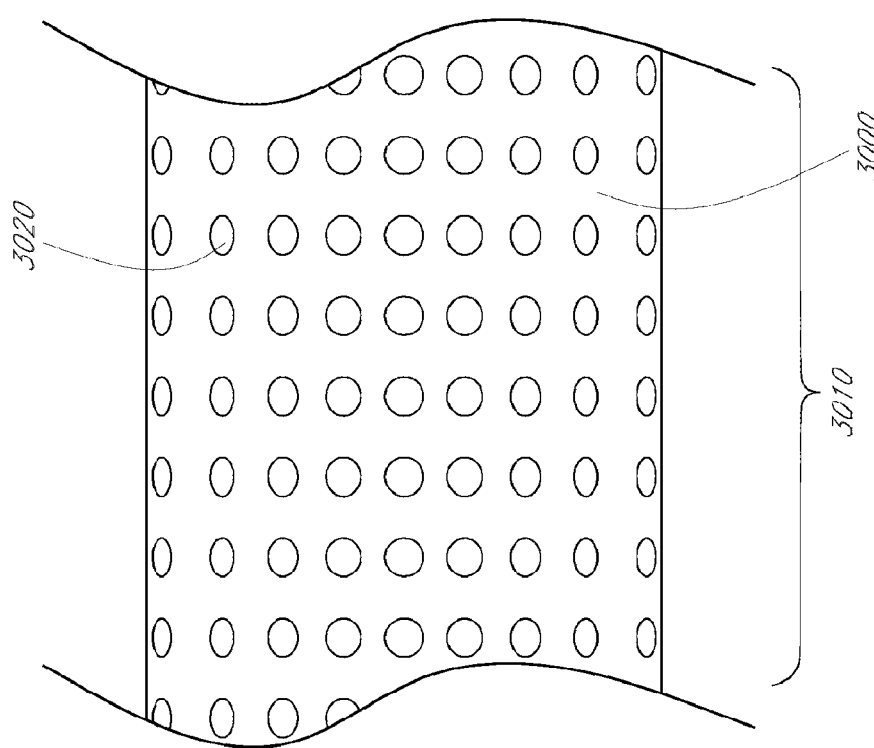

ULTRASOUND THERAPY SYSTEM

PRIORITY APPLICATION

This application is a divisional of U.S. patent application Ser. No. 11/739,629, filed Apr. 24, 2007, which claims the benefit of U.S. Provisional Application 60/794,330 (filed Apr. 24, 2006) and U.S. Provisional Application 60/799,119 (filed May 9, 2006), the entire contents of these applications are hereby incorporated by reference.

FIELD OF THE INVENTION

The present invention relates generally to treatment of vascular occlusions, and more specifically to treatment of vascular occlusions with ultrasonic energy and a therapeutic compound having microbubbles.

BACKGROUND OF THE INVENTION

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site within a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing therapeutic compounds directly to the occlusion site. Ultrasonic energy generated by the ultrasound assembly enhances the effect of the therapeutic compounds. Such a device can be used in the treatment of diseases such as ischemic stroke, peripheral arterial occlusion or deep vein thrombosis. In such applications, the ultrasonic energy enhances treatment of the occlusion with therapeutic compounds such as urokinase, tissue plasminogen activator ("tPA"), recombinant tissue plasminogen activator ("rtPA") and the like. Further information on enhancing the effect of a therapeutic compound using ultrasonic energy is provided in U.S. Pat. Nos. 5,318,014, 5,362,309, 5,474,531, 5,628,728, 6,001,069 and 6,210,356.

SUMMARY OF THE INVENTION

Certain therapeutic compounds contain a plurality of microbubbles having, for example, a gas formed therein. The efficacy of a therapeutic compound can be enhanced by the presence of the microbubbles contained therein. The microbubbles act as a nucleus for cavitation, which can help promote the dissolution and removal of a vascular occlusion. Furthermore, the mechanical agitation caused motion of the microbubbles can be effective in mechanically breaking up clot material. Therefore, ultrasound catheter systems configured for use with a microbubble-containing therapeutic compound have been developed.

In one embodiment of the present invention, a method of treating a vascular occlusion located at a treatment site within a patient's vasculature comprises positioning an ultrasound catheter at the treatment site. The method further comprises delivering a microbubble compound from the ultrasound catheter to the vascular occlusion while ultrasound is off during a first treatment phase. The method further comprises pausing the delivery of the microbubble compound and delivering ultrasonic energy and therapeutic compound or cooling fluid from the ultrasound catheter to the vascular occlusion during a second treatment phase while the delivery of microbubble compound remains paused.

In one embodiment of the present invention, a method of treating a vascular occlusion located at a treatment site within a patient's vasculature comprises passing an ultrasound catheter through the patient's vasculature to the treatment site. The ultrasound catheter includes at least one fluid delivery port. The method further comprises positioning the ultrasound catheter at the treatment site such that the at least one fluid delivery port is positioned within the occlusion. The method further comprises infusing a microbubble therapeutic compound from the ultrasound catheter into an internal portion of the occlusion. The method further comprises pausing delivery of the microbubble therapeutic compound from the ultrasound catheter after a first quantity has been infused into the occlusion. The method further comprises delivering ultrasonic energy and a therapeutic compound from the ultrasound catheter into the infused microbubble therapeutic compound. The method further comprises repositioning the ultrasound catheter at the treatment site. The method further comprises infusing a second quantity of microbubble therapeutic compound from the ultrasound catheter to the treatment site after the ultrasonic energy is delivered to the treatment site.

In one embodiment of the present invention, an ultrasound catheter system comprises an elongate tubular body having an ultrasound radiating member and a fluid delivery lumen positioned therein. The system further comprises a fluid reservoir that is hydraulically coupled to a proximal portion of the fluid delivery lumen. The fluid delivery reservoir contains a microbubble therapeutic compound. The system further comprises an infusion pump configured to pump the microbubble therapeutic compound from the fluid reservoir into the fluid delivery lumen. The system further comprises control circuitry configured to send electrical activation power to the infusion pump and to the ultrasound radiating member. The control circuitry is configured such that the infusion pump and the ultrasound radiating member are not activated simultaneously.

BRIEF DESCRIPTION OF THE DRAWINGS

Example embodiments of the vascular occlusion treatment system are illustrated in the accompanying drawings, which are for illustrative purposes only. The drawings comprise the following figures, in which like numerals indicate like parts.

FIG. 12A is a cross-sectional view of a distal end of an ultrasonic catheter configured for use within small vessels of a patient's vasculature.

FIG. 12B is a cross-sectional view of the ultrasonic catheter of FIG. 12A taken through line 12B-12B.

FIG. 15 is a schematic illustration of selected components of an example system that is capable of using a single controller to alternatively deliver ultrasonic energy and a microbubble therapeutic compound to an intravascular treatment site.

FIG. 16B illustrates a close up of a cavitation promoting surface.

DETAILED DESCRIPTION OF PREFERRED EMBODIMENTS

Figure 1:
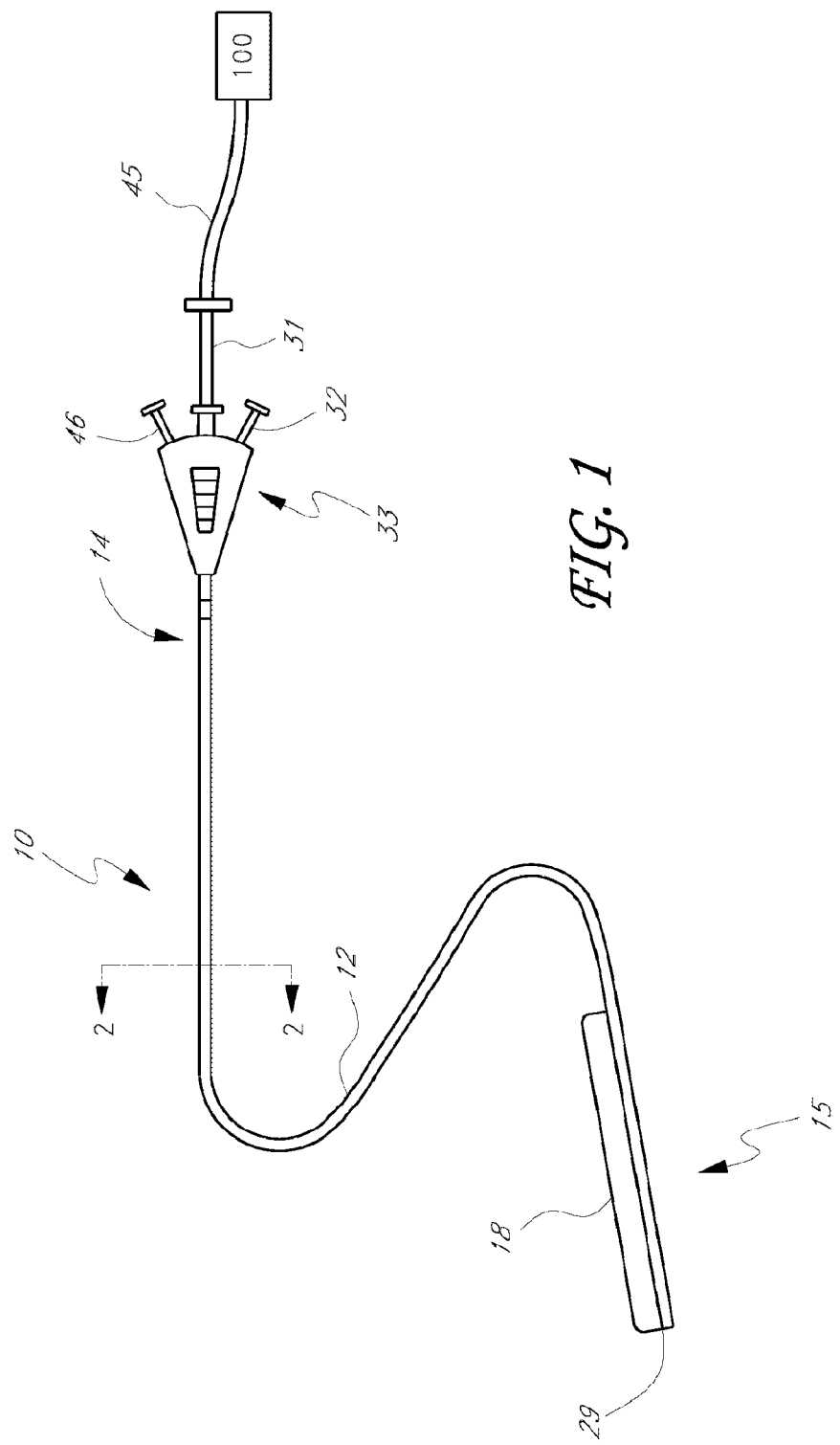
FIG. 1 is a schematic illustration of an ultrasonic catheter configured for insertion into large vessels of the human body.

As set forth above, methods and apparatuses have been developed that allow a vascular occlusion to be treated using both ultrasonic energy and a therapeutic compound having a controlled temperature. Disclosed herein are several example embodiments of ultrasonic catheters that can be used to enhance the efficacy of therapeutic compounds at a treatment site within a patient's body.

Introduction.

As used herein, the term "therapeutic compound" refers broadly, without limitation, and in addition to its ordinary meaning, to a drug, medicament, dissolution compound, genetic material, neuroprotection compounds or any other substance capable of effecting physiological functions. Additionally, a mixture includes substances such as these is also encompassed within this definition of "therapeutic compound". Examples of therapeutic compounds include thrombolytic compounds, anti-thrombosis compounds, and other compounds used in the treatment of vascular occlusions, including compounds intended to prevent or reduce clot formation. In applications where human blood vessels that have become partially or completely occluded by plaque, thrombi, emboli or other substances that reduce the blood carrying capacity of a vessel, example therapeutic compounds include, but are not limited to, heparin, urokinase, streptokinase, tPA, rtPA and BB-10153 (manufactured by British Biotech, Oxford, UK).

As used herein, the terms "ultrasonic energy", "ultrasound" and "ultrasonic" refer broadly, without limitation, and in addition to their ordinary meaning, to mechanical energy transferred through longitudinal pressure or compression waves. Ultrasonic energy can be emitted as continuous or pulsed waves, depending on the parameters of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy referred to herein has a frequency between about 20 kHz and about 20 MHz. For example, in one embodiment, the ultrasonic energy has a frequency between about 500 kHz and about 20 MHz. In another embodiment, the ultrasonic energy has a frequency between about 1 MHz and about 3 MHz. In yet another embodiment, the ultrasonic energy has a frequency of about 2 MHz. In certain embodiments described herein, the average acoustic power of the ultrasonic energy is between about 0.01 watts and 300 watts. In one embodiment, the average acoustic power is about 15 watts.

As used herein, the term "ultrasound radiating member" refers broadly, without limitation, and in addition to its ordinary meaning, to any apparatus capable of producing ultrasonic energy. An ultrasonic transducer, which converts electrical energy into ultrasonic energy, is an example of an ultrasound radiating member. An example ultrasonic transducer capable of generating ultrasonic energy from electrical energy is a piezoelectric ceramic oscillator. Piezoelectric ceramics typically comprise a crystalline material, such as quartz, that changes shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

In certain applications, the ultrasonic energy itself provides a therapeutic effect to the patient. Examples of such therapeutic effects include preventing or reducing stenosis and/or restenosis; tissue ablation, abrasion or disruption; promoting temporary or permanent physiological changes in intracellular or intercellular structures; and rupturing microballoons or micro-bubbles for therapeutic compound delivery. Further information about such methods can be found in U.S. Pat. Nos. 5,261,291 and 5,431,663.

The ultrasonic catheters described herein can be configured for application of ultrasonic energy over a substantial length of a body lumen, such as, for example, the larger vessels located in the leg. In other embodiments, the ultrasonic catheters described herein can be configured to be inserted into the small cerebral vessels, in solid tissues, in duct systems and in body cavities. In other embodiments, treatment with the ultrasonic catheter is performed outside the vascular system, such as within or at a tumor, in which the treatment is configured to kill malignant tissues by enhancing the delivery of a cancer drug to the tumor. Additional embodiments that can be combined with certain features and aspects of the embodiments described herein are described in U.S. patent application Ser. No. 10/291,891, filed 7 Nov. 2002, the entire disclosure of which is hereby incorporated herein by reference.

Overview of a Large Vessel Ultrasonic Catheter.

FIG. 1 schematically illustrates an ultrasonic catheter 10 configured for use in the large vessels of a patient's anatomy. For example, the ultrasonic catheter 10 illustrated in FIG. 1 can be used to treat long segment peripheral arterial occlusions, such as those in the vascular system of the leg.

As illustrated in FIG. 1, the ultrasonic catheter 10 generally includes a multi-component, elongate flexible tubular body 12 having a proximal region 14 and a distal region 15. The tubular body 12 includes a flexible energy delivery section 18 located in the distal region 15. The tubular body 12 and other components of the catheter 10 can be manufactured in accordance with a variety of techniques known to an ordinarily skilled artisan. Suitable materials and dimensions can be readily selected based on the natural and anatomical dimensions of the treatment site and on the desired percutaneous access site.

For example, in an example embodiment, the tubular body proximal region 14 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the tubular body proximal region 14 is reinforced by braiding, mesh or other constructions to provide increased kink resistance and ability to be pushed. For example, nickel titanium or stainless steel wires can be placed along or incorporated into the tubular body 12 to reduce kinking.

For example, in an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths can be used in other applications.

In an example embodiment, the tubular body energy delivery section 18 comprises a material that is thinner than the material comprising the tubular body proximal region 14. In another example embodiment, the tubular body energy delivery section 18 comprises a material that has a greater acoustic transparency than the material comprising the tubular body proximal region 14. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 comprises the same material or a material of the same thickness as the proximal region 18.

In an example embodiment, the tubular body 12 is divided into at least three sections of varying stiffness. The first section, which includes the proximal region 14, has a relatively higher stiffness. The second section, which is located in an intermediate region between the proximal region 14 and the distal region 15, has a relatively lower stiffness. This configuration further facilitates movement and placement of the catheter 10. The third section, which includes the energy delivery section 18, has a relatively lower stiffness than the second section in spite of the presence of ultrasound radiating members which can be positioned therein.

Figure 2:
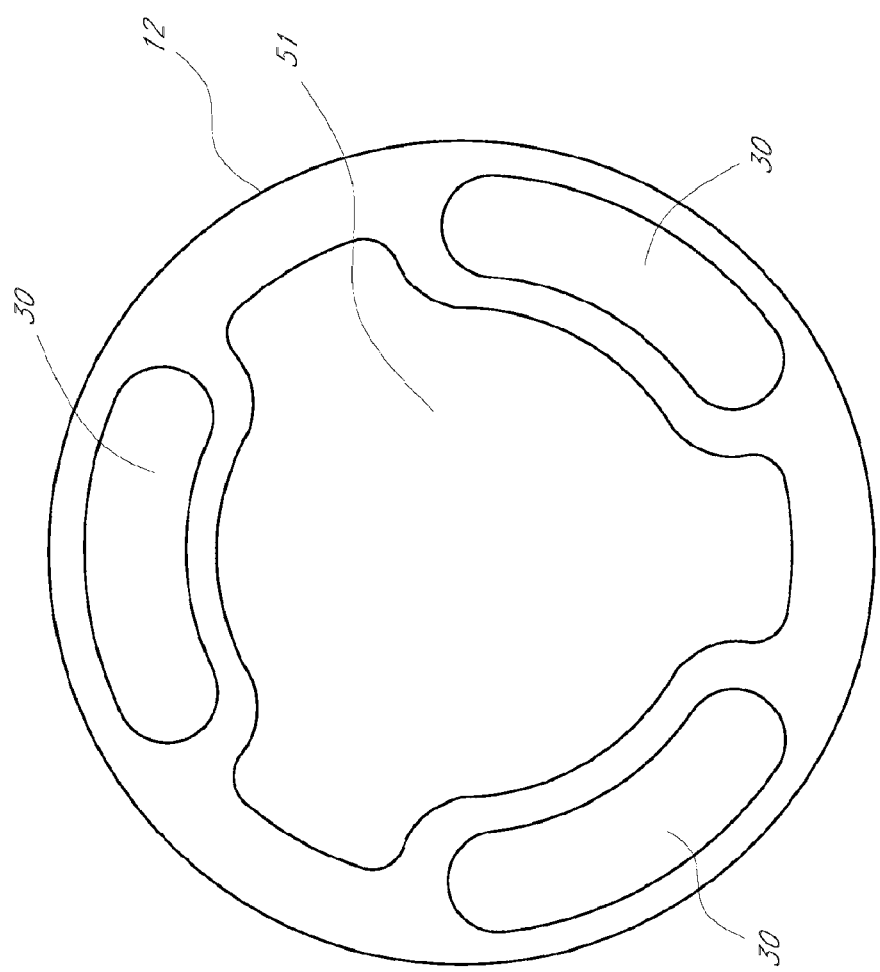
FIG. 2 is a cross-sectional view of the ultrasonic catheter of FIG. 1 taken along line 2-2.

FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. In such embodiments, the arrangement of the fluid delivery lumens 30 provides a hollow central lumen 51 passing through the tubular body 12. The cross-section of the tubular body 12, as illustrated in FIG. 2, is substantially constant along the length of the catheter 10. Thus, in such embodiments, substantially the same cross-section is present in both the proximal region 14 and the distal region 15 of the tubular body 12, including the energy delivery section 18.

In certain embodiments, the central lumen 51 has a minimum diameter greater than about 0.030 inches. In another embodiment, the central lumen 51 has a minimum diameter greater than about 0.037 inches. In an example embodiment, the fluid delivery lumens 30 have dimensions of about 0.026 inches wide by about 0.0075 inches high, although other dimensions can be used in other embodiments.

In an example embodiment, the central lumen 51 extends through the length of the tubular body 12. As illustrated in FIG. 1, the central lumen 51 has a distal exit port 29 and a proximal access port 31. The proximal access port 31 forms part of the backend hub 33, which is attached to the tubular body proximal region 14. In such embodiments, the backend hub also includes a cooling fluid fitting 46, which is hydraulically connected to the central lumen 51. In such embodiments, the backend hub 33 also includes a therapeutic compound inlet port 32, which is hydraulically coupled to the fluid delivery lumens 30, and which can also be hydraulically coupled to a source of therapeutic compound via a hub such as a Luer fitting.

Figure 3:
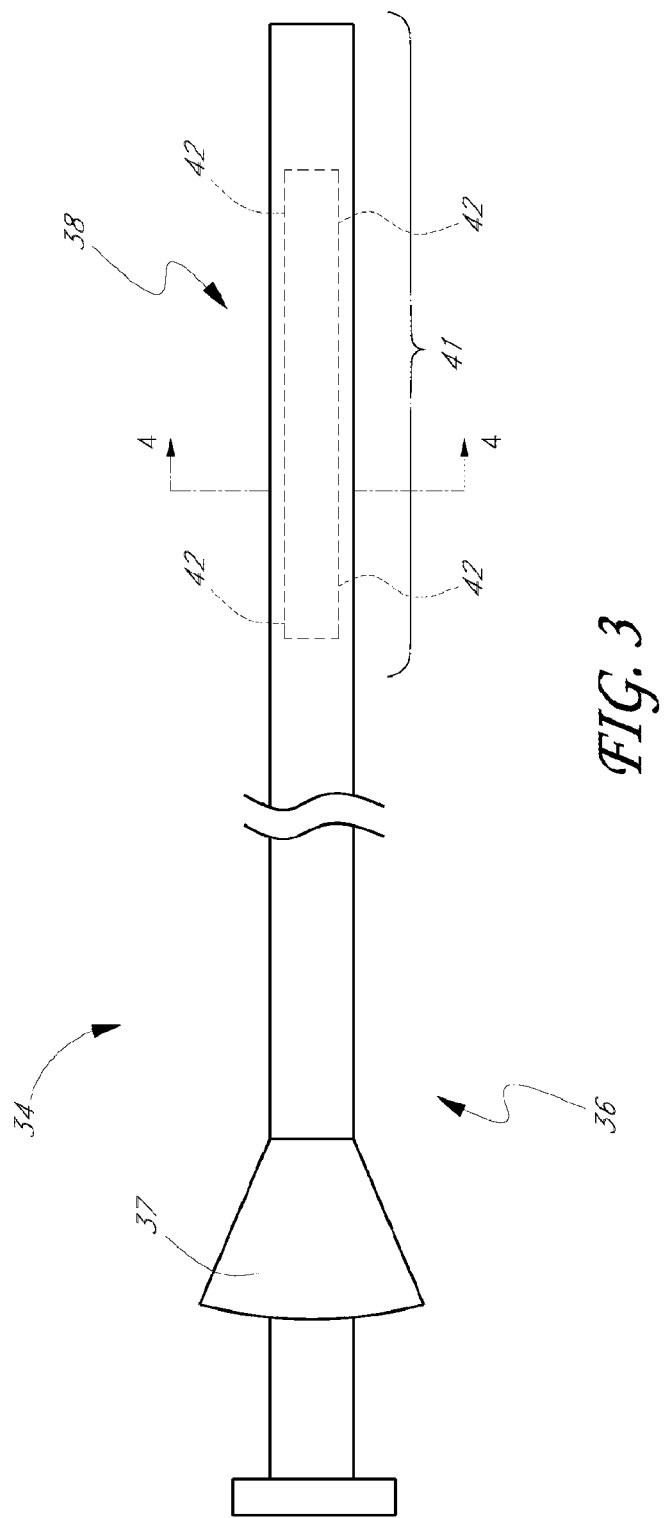
FIG. 3 is a schematic illustration of an elongate inner core configured to be positioned within the central lumen of the catheter illustrated in FIG. 2.

The central lumen 51 is configured to receive an elongate inner core 34, an example embodiment of which is illustrated in FIG. 3. In such embodiments, the elongate inner core 34 includes a proximal region 36 and a distal region 38. A proximal hub 37 is fitted on one end of the inner core proximal region 36. One or more ultrasound radiating members 40 are positioned within an inner core energy delivery section 41 that is located within the distal region 38. The ultrasound radiating members 40 form an ultrasound assembly 42, which will be described in greater detail below.

Figure 4:
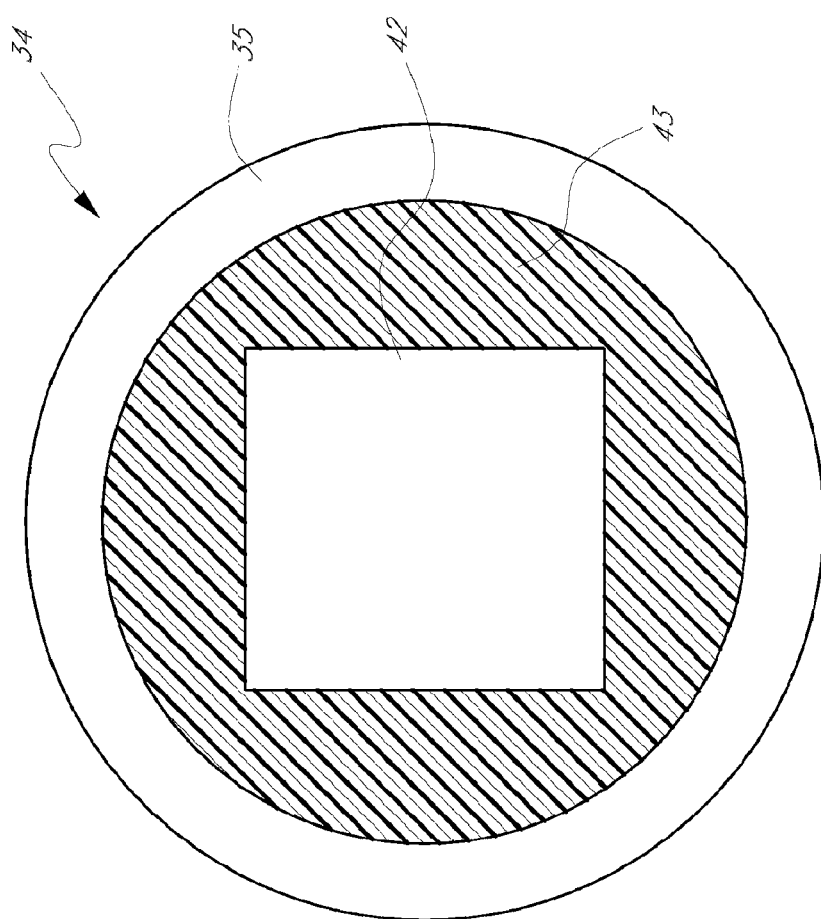
FIG. 4 is a cross-sectional view of the elongate inner core of FIG. 3 taken along line 4-4.

As shown in the cross-section illustrated in FIG. 4, which is taken along lines 4-4 in FIG. 3, in an example embodiment, the inner core 34 has a cylindrical shape, with an outer diameter that permits the inner core 34 to be inserted into the central lumen 51 of the tubular body 12 via the proximal access port 31. Suitable outer diameters of the inner core 34 include, but are not limited to, between about 0.010 inches and about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 includes a cylindrical outer body 35 that houses the ultrasound assembly 42. The ultrasound assembly 42 includes wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to a control system 100 via cable 45 (illustrated in FIG. 1). In an example embodiment, an electrically insulating potting material 43 fills the inner core 34, surrounding the ultrasound assembly 42, thus reducing or preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
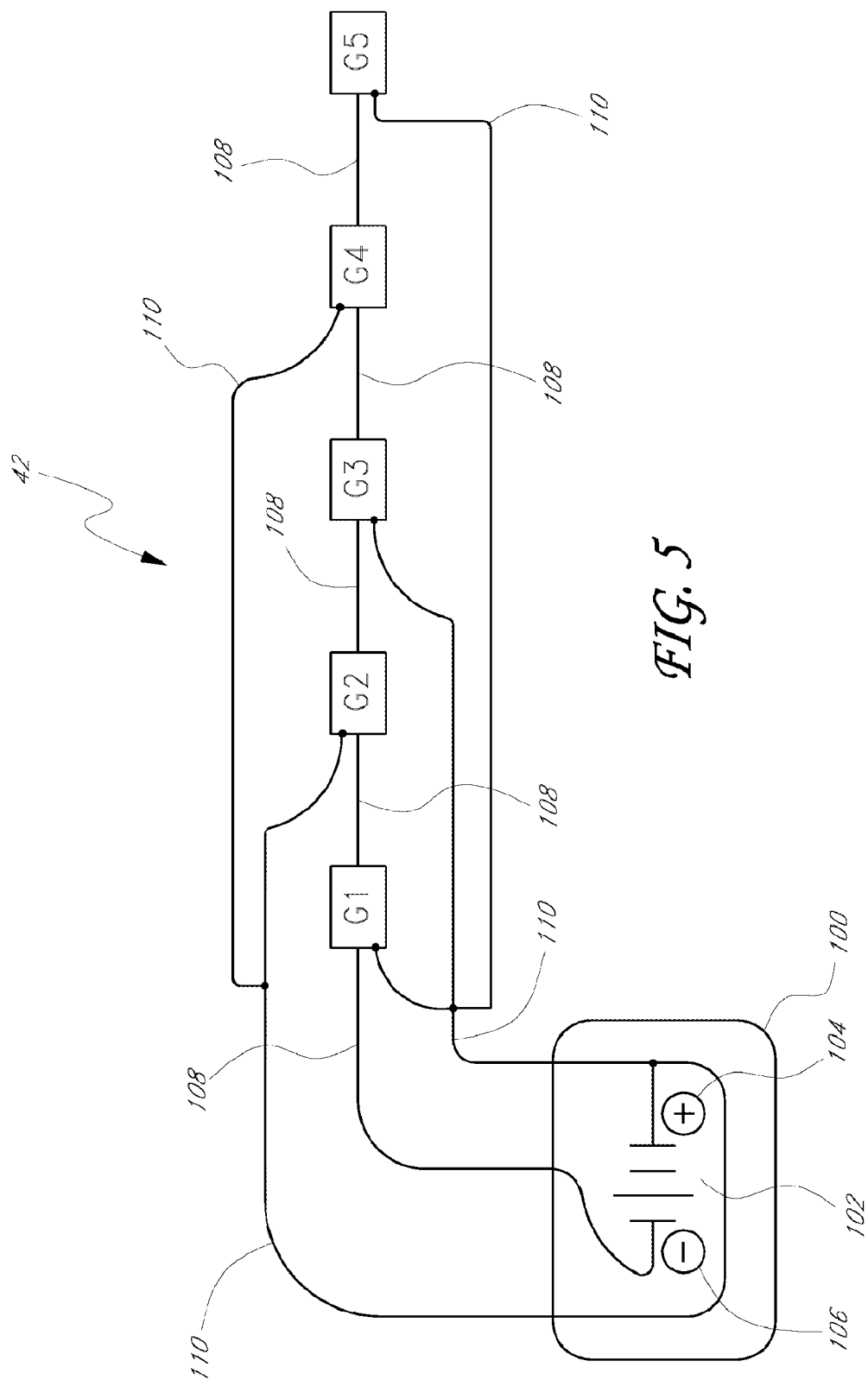
FIG. 5 is a schematic wiring diagram illustrating an example technique for electrically connecting five groups of ultrasound radiating members to form an ultrasound assembly.
Figure 6:
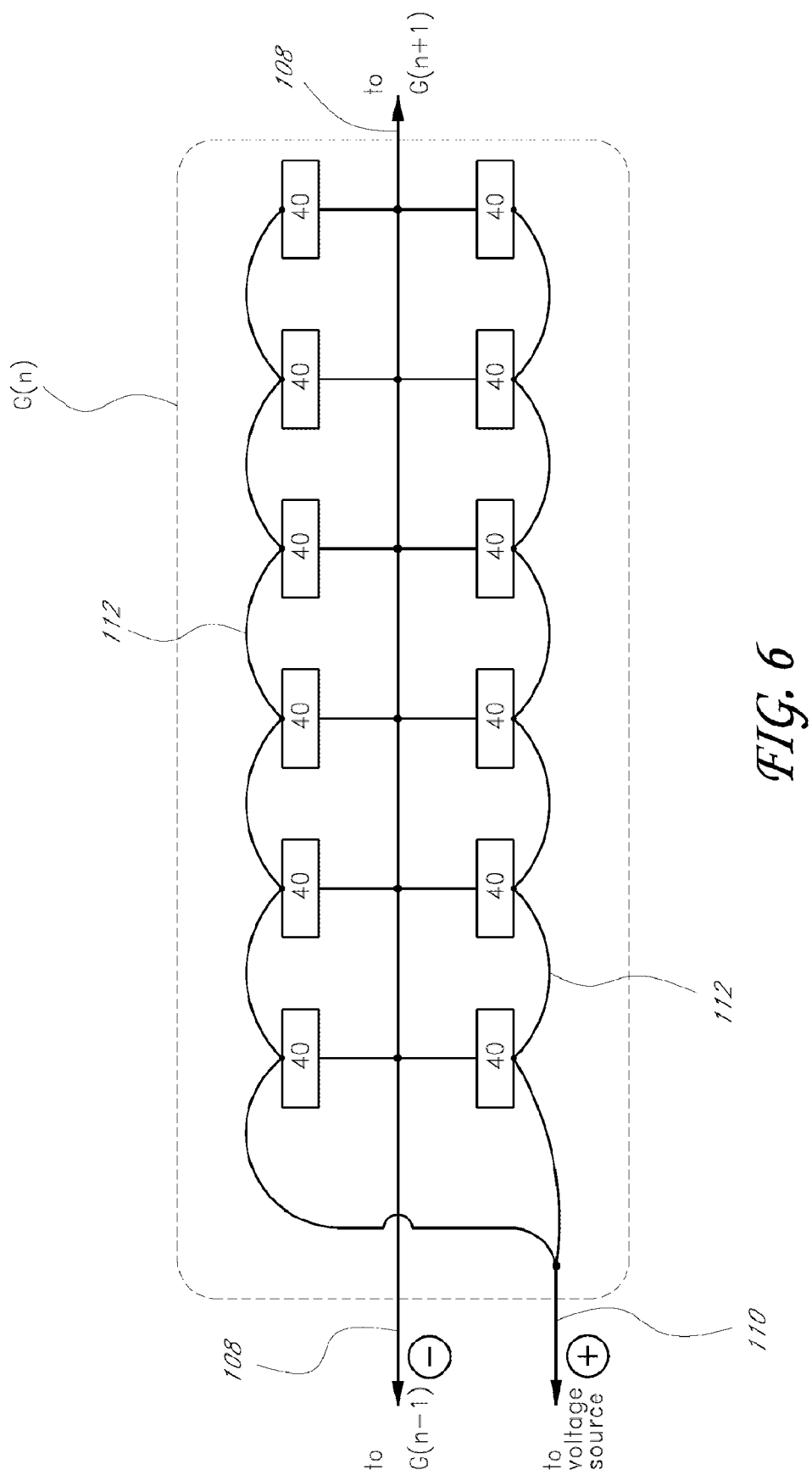
FIG. 6 is a schematic wiring diagram illustrating an example technique for electrically connecting one of the groups of FIG. 5.

In an example embodiment, the ultrasound assembly 42 includes a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control system 100.

Still referring to FIG. 5, in an example embodiment, the control circuitry 100 includes a voltage source 102 having a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 6, is connected to the positive terminal 104 via one of the lead wires 110, and to the negative terminal 106 via the common wire 108.

Referring now to FIG. 6, each group G1-G5 includes a plurality of ultrasound radiating members 40. Each of the ultrasound radiating members 40 is electrically connected to the common wire 108 and to the lead wire 110 via a positive contact wires 112. Thus, when wired as illustrated, a substantially constant voltage difference will be applied to each ultrasound radiating member 40 in the group. Although the group illustrated in FIG. 6 includes twelve ultrasound radiating members 40, in other embodiments, more or fewer ultrasound radiating members 40 can be included in the group. Likewise, more or fewer than five groups can be included within the ultrasound assembly 42 illustrated in FIG. 5.

Figure 7A:
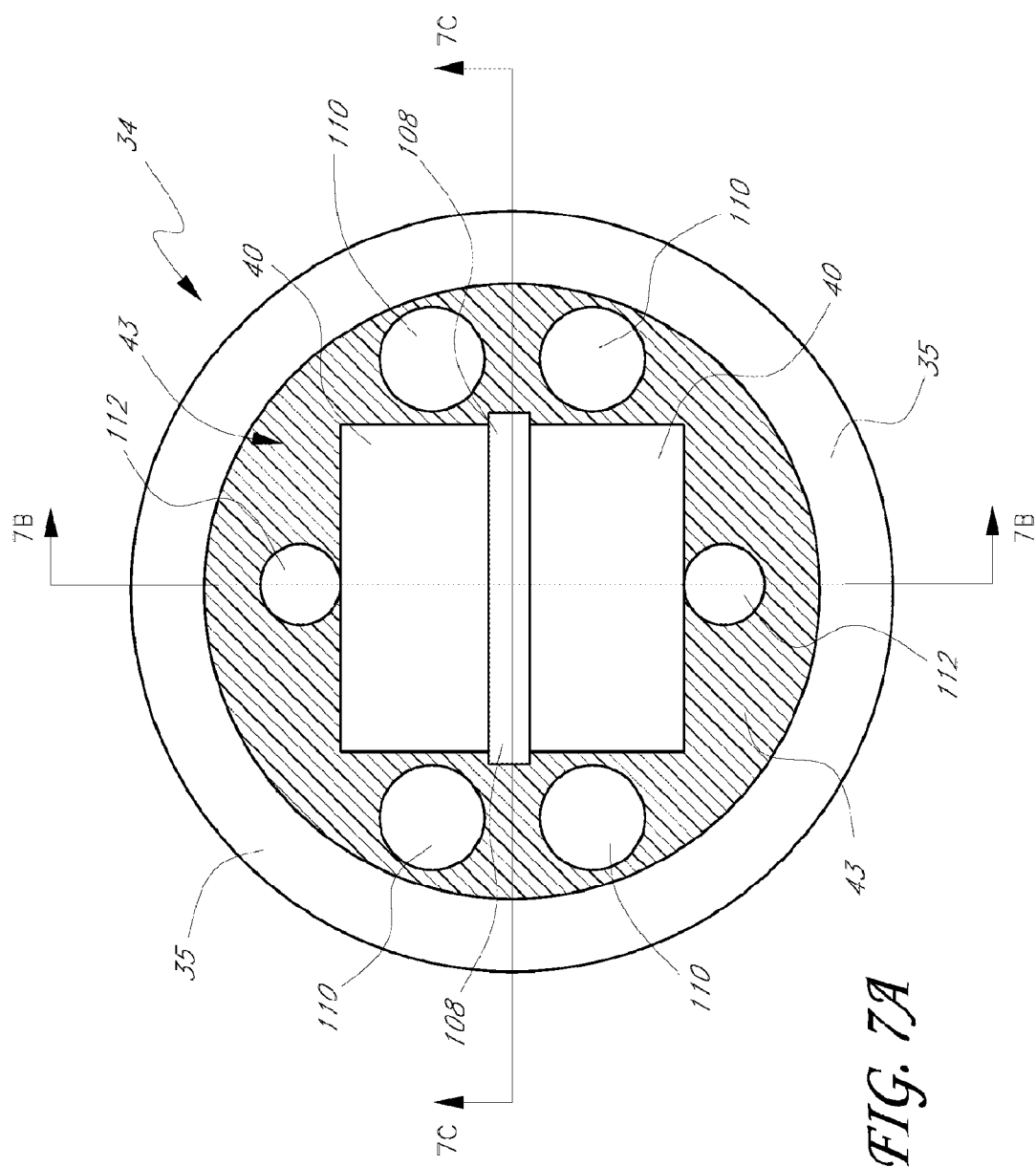
FIG. 7A is a schematic illustration of the ultrasound assembly of FIG. 5 housed within the inner core of FIG. 4.

FIG. 7A illustrates an example technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

In the example embodiment illustrated in FIG. 7A, the common wire 108 includes an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. In such embodiments, lead wires 110 are separated from the other components of the ultrasound assembly 42, thus preventing interference with the operation of the ultrasound radiating members 40 as described above. For example, in an example embodiment, the inner core 34 is filled with an insulating potting material 43, thus deterring unwanted electrical contact between the various components of the ultrasound assembly 42.

Figure 7B:
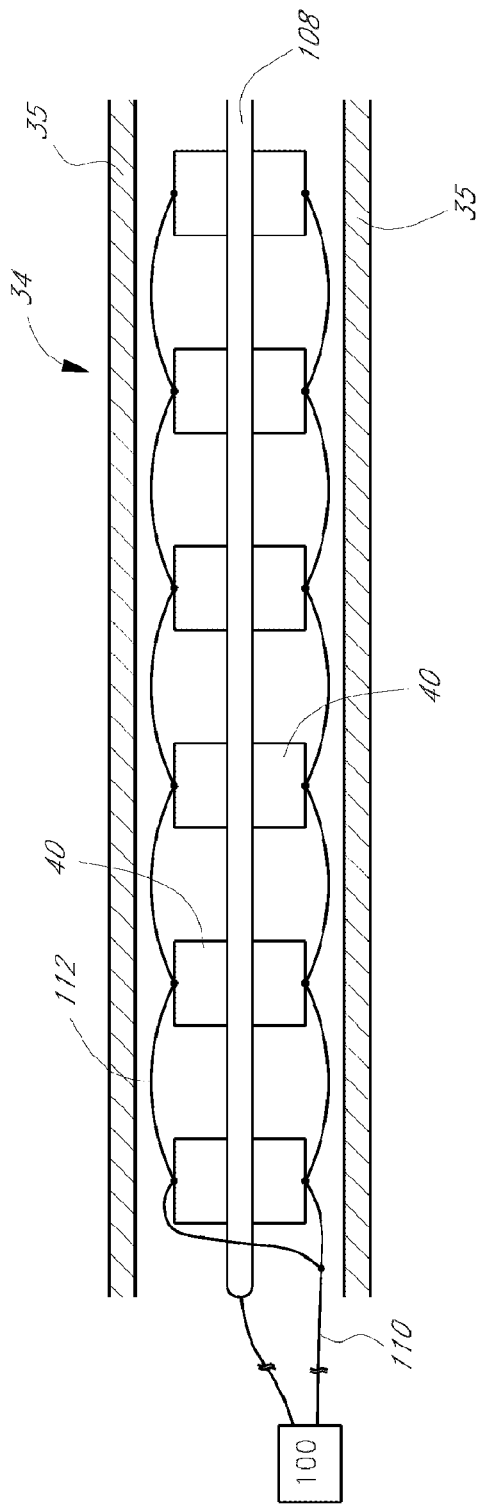
FIG. 7B is a cross-sectional view of the ultrasound assembly of FIG. 7A taken along line 7B-7B.
Figure 7C:
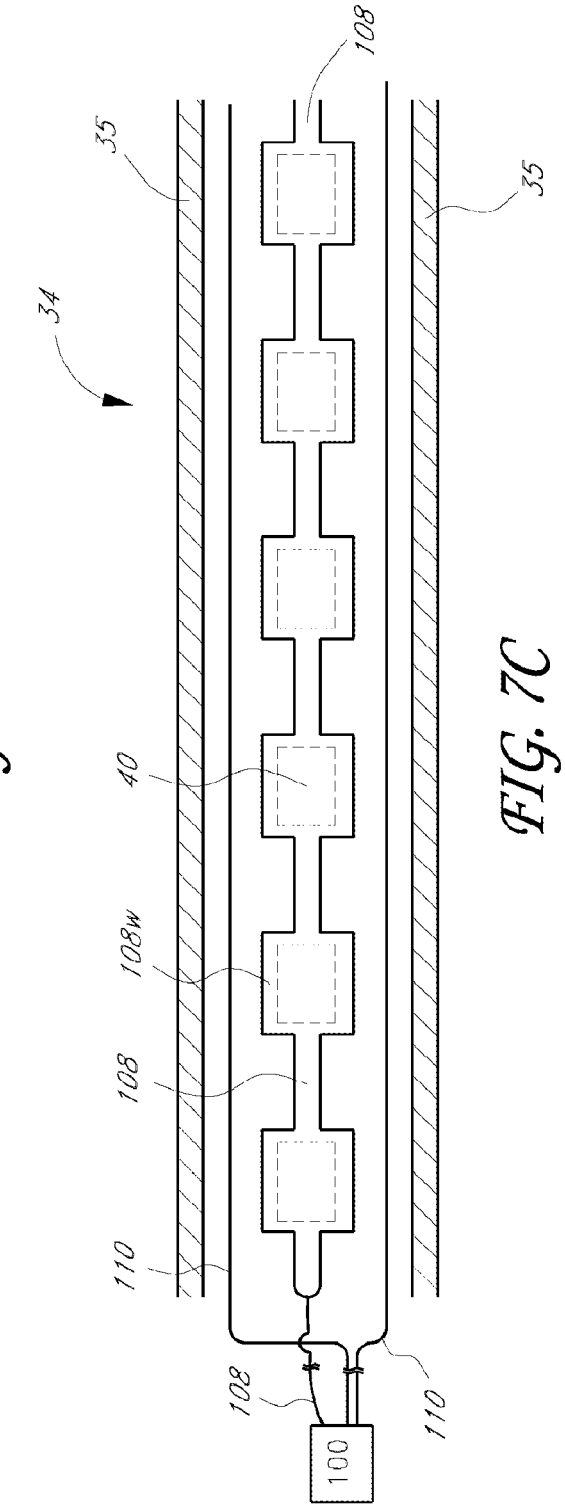
FIG. 7C is a cross-sectional view of the ultrasound assembly of FIG. 7A taken along line 7C-7C.

FIGS. 7B and 7C illustrate cross sectional views of the inner core 34 of FIG. 7A taken along lines 7B-7B and 7C-7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 includes wide regions 108W upon which the ultrasound radiating members 40 can be mounted, thus reducing the likelihood that the paired ultrasound radiating members 40 will short together. In certain embodiments, outside the wide regions 108W, the common wire 108 can have a more conventional, rounded wire shape.

Figure 7D:
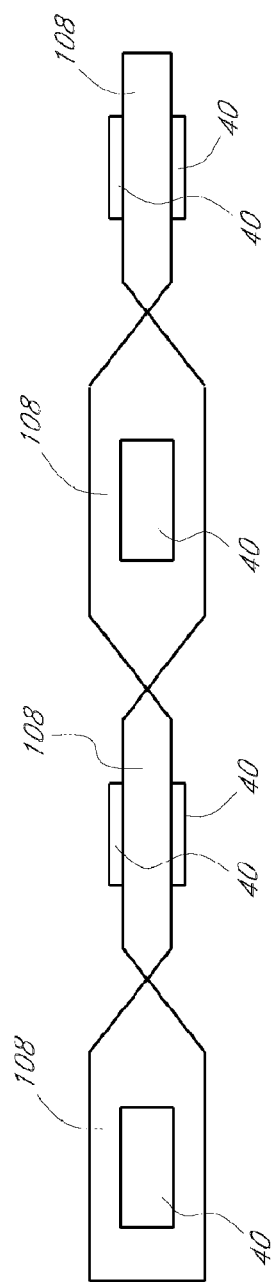
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

The wiring arrangement described above can be modified to allow each group G1, G2, G3, G4, G5 to be independently powered. Specifically, by providing a separate power source within the control system 100 for each group, each group can be individually turned on or off, or can be driven at an individualized power level. This advantageously allows the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, include a plurality of ultrasound radiating members grouped spatially. That is, in such embodiments, the ultrasound radiating members within a certain group are positioned adjacent to each other, such that when a single group is activated, ultrasonic energy is delivered from a certain length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the ultrasound assembly. Such modified embodiments can be advantageous in applications where a less focussed, more diffuse ultrasonic energy field is to be delivered to the treatment site.

In an example embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configurations and dimensions can be used. For example, disc-shaped ultrasound radiating members 40 can be used in other embodiments. In an example embodiment, the common wire 108 comprises copper, and is about 0.005 inches thick, although other electrically conductive materials and other dimensions can be used in other embodiments. In an example embodiment, lead wires 110 are 36 gauge electrical conductors, and positive contact wires 112 are 42 gauge electrical conductors. However, other wire gauges can be used in other embodiments.

As described above, suitable frequencies for the ultrasound radiating members 40 include, but are not limited to, from about 20 kHz to about 20 MHz. In one embodiment, the frequency is between about 500 kHz and about 20 MHz, and in another embodiment the frequency is between about 1 MHz and about 3 MHz. In yet another embodiment, the ultrasound radiating members 40 are operated with a frequency of about 2 MHz.

Figure 8:
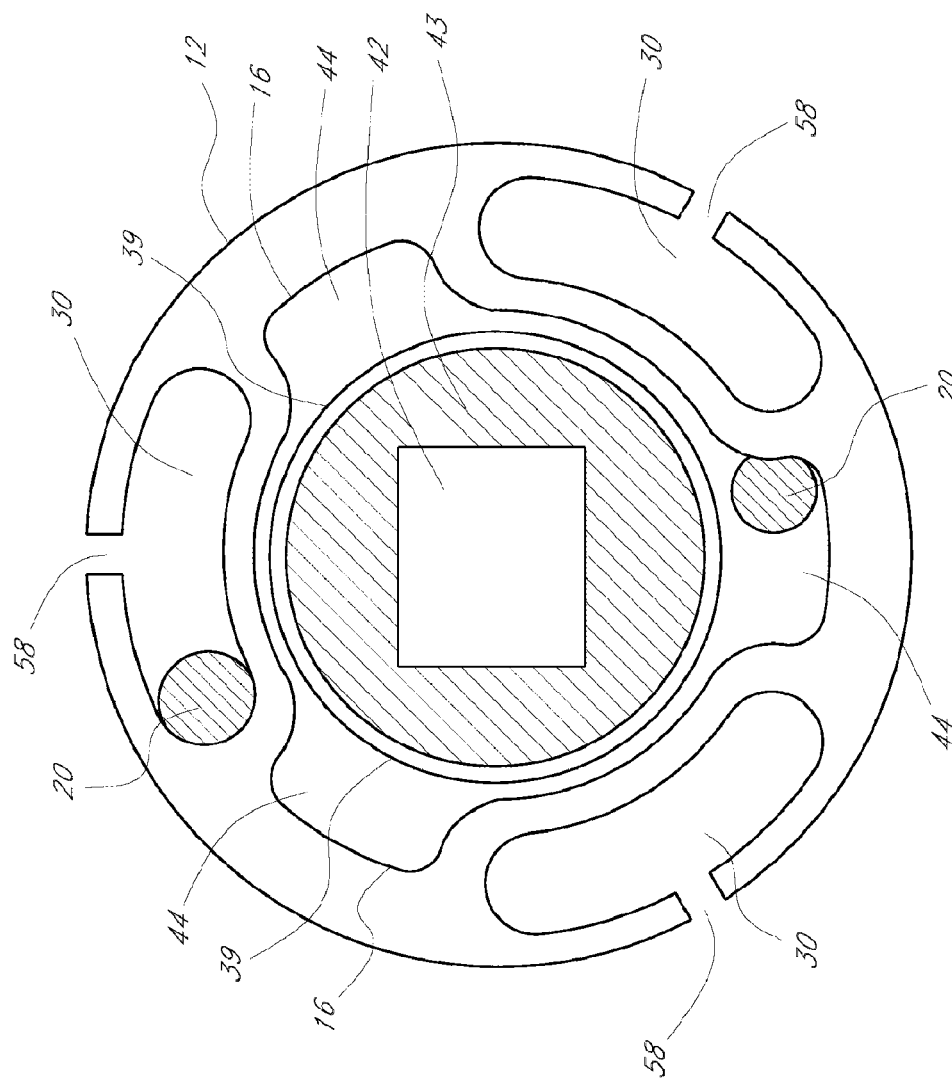
FIG. 8 illustrates the energy delivery section of the inner core of FIG. 4 positioned within the energy delivery section of the tubular body of FIG. 2.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in an example embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. A plurality of fluid delivery ports 58 can be positioned axially along the tubular body 12. Thus, a source of therapeutic compound coupled to the inlet port 32 provides a hydraulic pressure which drives the therapeutic compound through the fluid delivery lumens 30 and out the fluid delivery ports 58.

By spacing the fluid delivery lumens 30 around the circumference of the tubular body 12 substantially evenly, as illustrated in FIG. 8, a substantially uniform flow of therapeutic compound around the circumference of the tubular body 12 can be achieved. Additionally, the size, location and geometry of the fluid delivery ports 58 can be selected to provide uniform fluid flow from the fluid delivery ports 30 to the treatment site. For example, in one embodiment, fluid delivery ports closer to the proximal region of the energy delivery section 18 have smaller diameters than fluid delivery ports closer to the distal region of the energy delivery section 18, thereby allowing uniform delivery of therapeutic compound in the energy delivery section.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to about 0.0020 inches in the distal region of the energy delivery section 18. The increase in size between adjacent fluid delivery ports 58 depends on a variety of factors, including the material comprising the tubular body 12, and on the size of the fluid delivery lumen 30. The fluid delivery ports 58 can be created in the tubular body 12 by punching, drilling, burning or ablating (such as with a laser), or by other suitable methods. Therapeutic compound flow along the length of the tubular body 12 can also be increased by increasing the density of the fluid delivery ports 58 toward the distal region of the energy delivery section.

In certain applications, a spatially nonuniform flow of therapeutic compound from the fluid delivery ports 58 to the treatment site is to be provided. In such applications, the size, location and geometry of the fluid delivery ports 58 can be selected to provide such nonuniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flows through cooling fluid lumens 44 and out of the catheter 10 through distal exit port 29 (see FIG. 1). In an example embodiment, the cooling fluid lumens 44 are substantially evenly spaced around the circumference of the tubular body 12 (that is, at approximately 120° increments for a three-lumen configuration), thereby providing substantially uniform cooling fluid flow over the inner core 34. Such a configuration advantageously removes thermal energy from the treatment site. As will be explained below, the flow rate of the cooling fluid and the power to the ultrasound assembly 42 can be adjusted to maintain the temperature of the inner core energy delivery section 41, or of the treatment site generally, within a desired range.

In an example embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, in an example embodiment, the inner core outer body 35 comprises a material having the ability to transmit torque. Suitable materials for the inner core outer body 35 include, but are not limited to, polyimides, polyesters, polyurethanes, thermoplastic elastomers and braided polyimides.

In an example embodiment, the fluid delivery lumens 30 and the cooling fluid lumens 44 are open at the distal end of the tubular body 12, thereby allowing the therapeutic compound and the cooling fluid to pass into the patient's vasculature at the distal exit port 29. In a modified embodiment, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can be prevented from passing through the distal exit port 29 by providing the inner core 34 with a length that is less than the length of the tubular body 12. In other embodiments, a protrusion is formed within the tubular body 12 in the distal region 15, thereby preventing the inner core 34 from passing through the distal exit port 29.

In other embodiments, the catheter 10 includes an occlusion device positioned at the distal exit port 29. In such embodiments, the occlusion device has a reduced inner diameter that can accommodate a guidewire, but that is less than the inner diameter of the central lumen 51. Thus, the inner core 34 is prevented from extending past the occlusion device and out the distal exit port 29. For example, suitable inner diameters for the occlusion device include, but are not limited to, between about 0.005 inches and about 0.050 inches. In other embodiments, the occlusion device has a closed end, thus preventing cooling fluid from leaving the catheter 10, and instead recirculating to the tubular body proximal region 14. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In an example embodiment, such as illustrated in FIG. 8, the tubular body 12 includes one or more temperature sensors 20 that are positioned within the energy delivery section 18. In such embodiments, the tubular body proximal region 14 includes a temperature sensor lead which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44.

Figure 9:
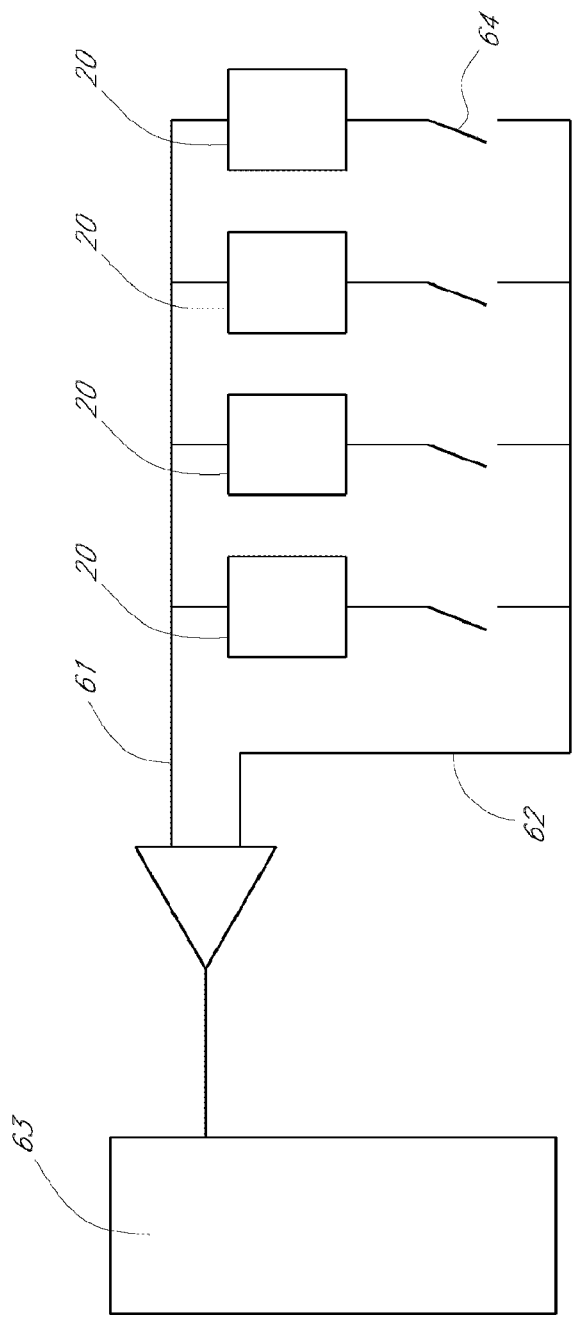
FIG. 9 illustrates a wiring diagram for connecting a plurality of temperature sensors with a common wire.

FIG. 9 illustrates an example embodiment for electrically connecting the temperature sensors 20. In such embodiments, each temperature sensor 20 is coupled to a common wire 61 and is associated with an individual return wire 62. Accordingly, n+1 wires are passed through the tubular body 12 to independently sense the temperature at n temperature sensors 20. The temperature at a selected temperature sensor 20 can be determined by closing a switch 64 to complete a circuit between the return wire 62 associated with the selected thermocouple and the common wire 61. In embodiments wherein the temperature sensors 20 are thermocouples, the temperature can be calculated from the voltage in the circuit using, for example, a sensing circuit 63, which can be located within the external control circuitry 100.

In other embodiments, the temperature sensors 20 can be independently wired. In such embodiments, 2n wires are passed through the tubular body 12 to independently sense the temperature at n temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
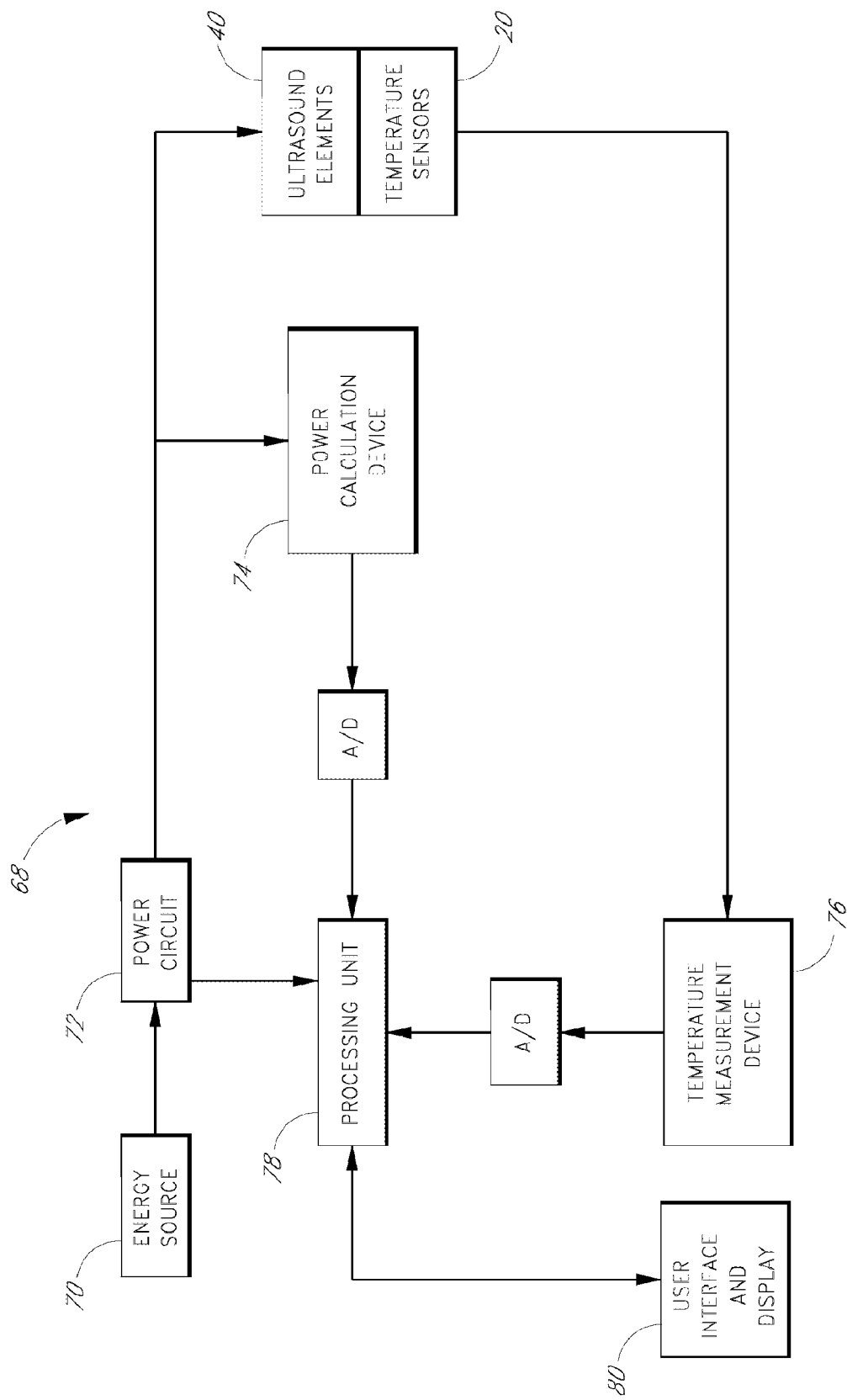
FIG. 10 is a block diagram of a feedback control system for use with an ultrasonic catheter.

FIG. 10 schematically illustrates one embodiment of a feedback control system 68 that can be used with the catheter 10. The feedback control system 68 can be integrated into the control system 100 that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

In an example embodiment, the feedback control system 68 includes an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In an example method of operation, the temperature at each temperature sensor 20 is determined by the temperature measurement device 76. The processing unit 78 receives each determined temperature from the temperature measurement device 76. The determined temperature can then be displayed to the user at the user interface and display 80.

In an example embodiment, the processing unit 78 includes logic for generating a temperature control signal. The temperature control signal is proportional to the difference between the measured temperature and a desired temperature. The desired temperature can be determined by the user (as set at the user interface and display 80) or can be preset within the processing unit 78.

In such embodiments, the temperature control signal is received by the power circuits 72. The power circuits 72 are configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is reduced in response to that temperature control signal. Similarly, when the temperature control signal is below a particular level, the power supplied to a particular group of ultrasound radiating members 40 is increased in response to that temperature control signal. After each power adjustment, the processing unit 78 monitors the temperature sensors 20 and produces another temperature control signal which is received by the power circuits 72.

In an example embodiment, the processing unit 78 optionally includes safety control logic. The safety control logic detects when the temperature at a temperature sensor 20 exceeds a safety threshold. In this case, the processing unit 78 can be configured to provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating members 40 can be identically adjusted in certain embodiments. For example, in a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 can also be configured to receive a power signal from the power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, in certain applications, tissue at the treatment site is to have a temperature increase of less than or equal to approximately 6° C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as a computer with software. In embodiments wherein the processing unit 78 is a computer, the computer can include a central processing unit ("CPU") coupled through a system bus. In such embodiments, the user interface and display 80 can include a mouse, a keyboard, a disk drive, a display monitor, a nonvolatile memory system, and/or other computer components. In an example embodiment, program memory and/or data memory is also coupled to the bus.

In another embodiment, in lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 is provided according to the preset profiles.

In an example embodiment, the ultrasound radiating members are operated in a pulsed mode. For example, in one embodiment, the time average power supplied to the ultrasound radiating members is between about 0.1 watts and about 2 watts. In another embodiment, the time average power supplied to the ultrasound radiating members is between about 0.5 watts and about 1.5 watts. In yet another embodiment, the time average power supplied to the ultrasound radiating members is approximately 0.6 watts or approximately 1.2 watts. In an example embodiment, the duty cycle is between about 1% and about 50%. In another embodiment, the duty cycle is between about 5% and about 25%. In yet another embodiment, the duty cycles is approximately 7.5% or approximately 15%. In an example embodiment, the pulse averaged power is between about 0.1 watts and about 20 watts. In another embodiment, the pulse averaged power is between approximately 5 watts and approximately 20 watts. In yet another embodiment, the pulse averaged power is approximately 8 watts or approximately 16 watts. The amplitude during each pulse can be constant or varied.

In an example embodiment, the pulse repetition rate is between about 5 Hz and about 150 Hz. In another embodiment, the pulse repetition rate is between about 10 Hz and about 50 Hz. In yet another embodiment, the pulse repetition rate is approximately 30 Hz. In an example embodiment, the pulse duration is between about 1 millisecond and about 50 milliseconds. In another embodiment, the pulse duration is between about 1 millisecond and about 25 milliseconds. In yet another embodiment, the pulse duration is approximately 2.5 milliseconds or approximately 5 milliseconds.

For example, in one particular embodiment, the ultrasound radiating members are operated at an average power of approximately 0.6 watts, a duty cycle of approximately 7.5%, a pulse repetition rate of approximately 30 Hz, a pulse average electrical power of approximately 8 watts and a pulse duration of approximately 2.5 milliseconds.

In an example embodiment, the ultrasound radiating member used with the electrical parameters described herein has an acoustic efficiency greater than approximately 50%. In another embodiment, the ultrasound radiating member used with the electrical parameters described herein has an acoustic efficiency greater than approximately 75%. As described herein, the ultrasound radiating members can be formed in a variety of shapes, such as, cylindrical (solid or hollow), flat, bar, triangular, and the like. In an example embodiment, the length of the ultrasound radiating member is between about 0.1 cm and about 0.5 cm, and the thickness or diameter of the ultrasound radiating member is between about 0.02 cm and about 0.2 cm.

Figure 11A:
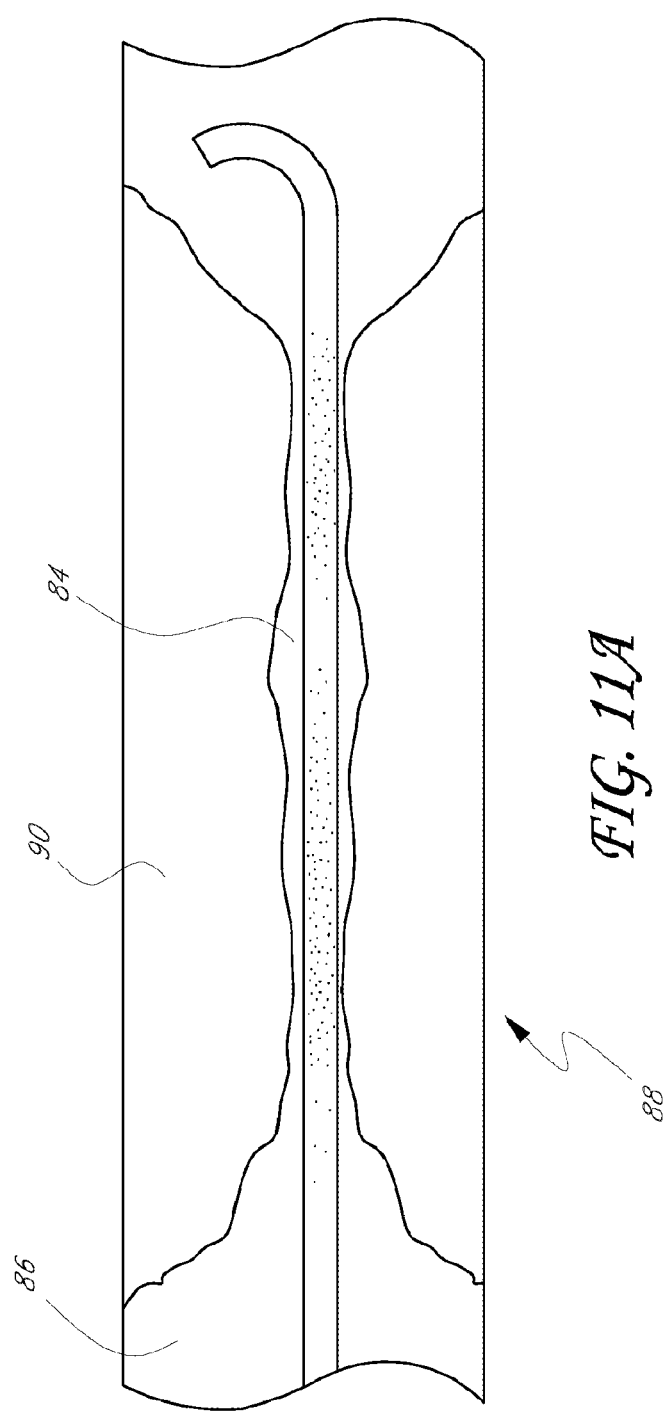
FIG. 11A is a side view of a treatment site.

FIGS. 11A through 11D illustrate an example method for using certain embodiments of the ultrasonic catheter 10 describe herein. As illustrated in FIG. 11A, a guidewire 84 similar to a guidewire used in typical angioplasty procedures is directed through a patient's vessels 86 to a treatment site 88 that includes a clot 90. The guidewire 84 is optionally directed through the clot 90. Suitable vessels 86 include, but are not limited to, the large periphery blood vessels of the body. Additionally, as mentioned above, the ultrasonic catheter 10 also has utility in various imaging applications or in applications for treating and/or diagnosing other diseases in other body parts.

Figure 11B:
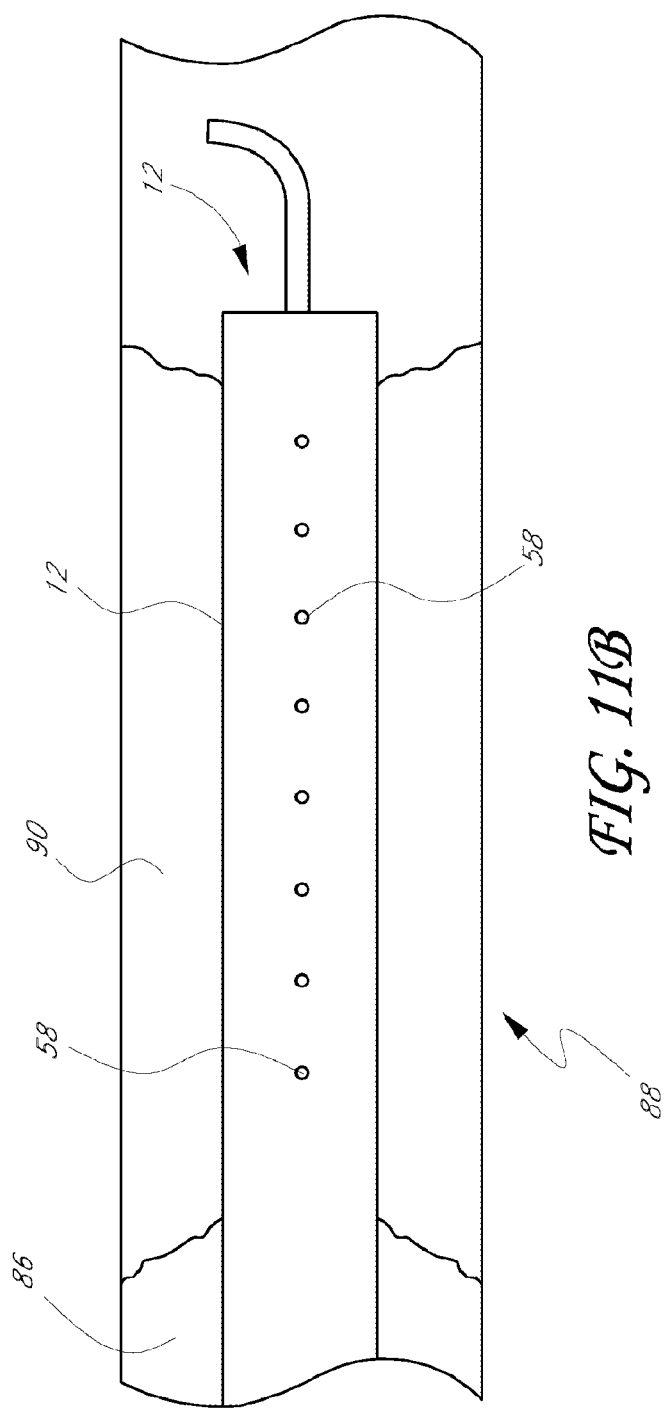
FIG. 11B is a side view of the distal end of an ultrasonic catheter positioned at the treatment site of FIG. 11A.
Figure 11C:
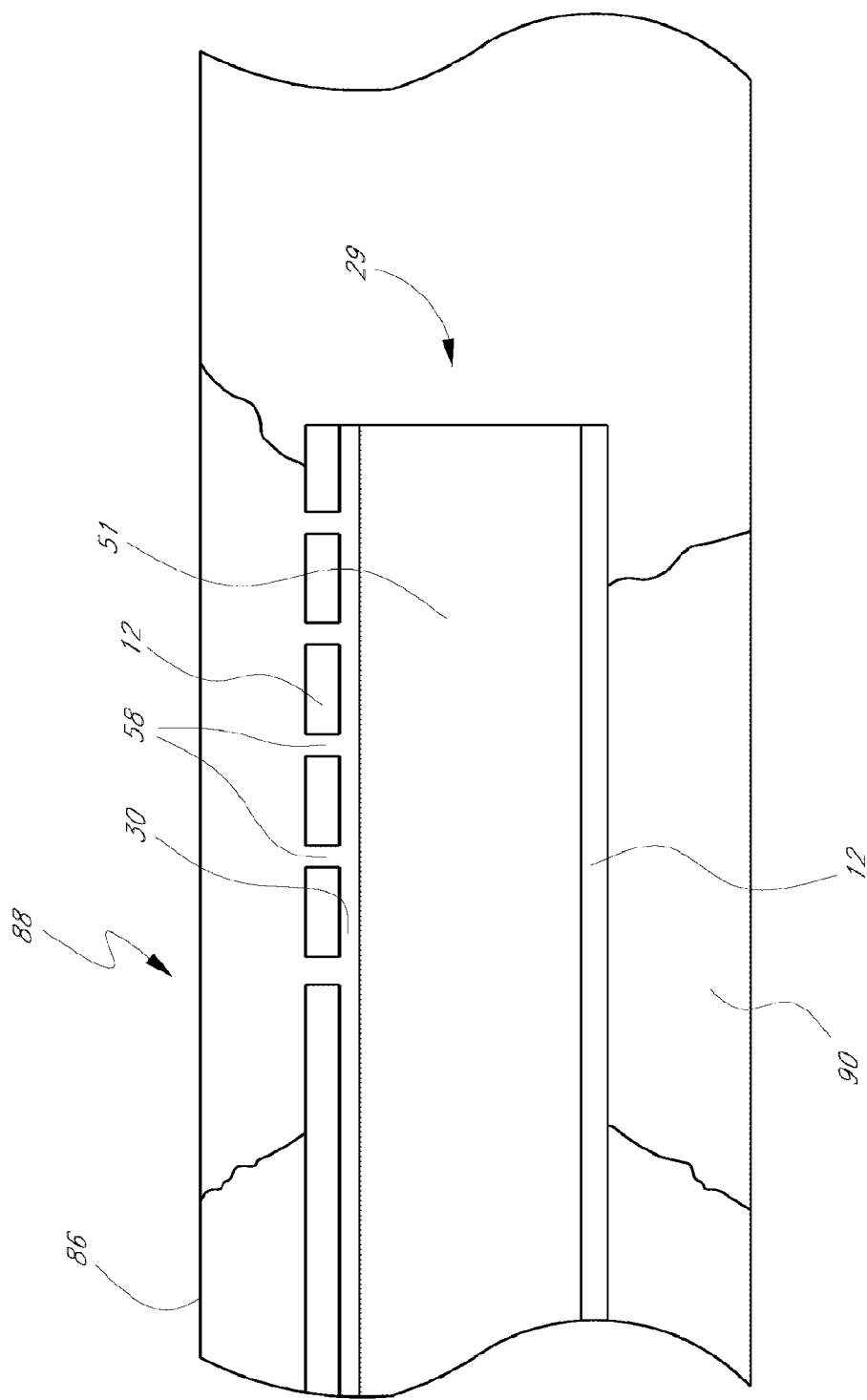
FIG. 11C is a cross-sectional view of the distal end of the ultrasonic catheter of FIG. 11B positioned at the treatment site before a treatment.

As illustrated in FIG. 11B, the tubular body 12 is slid over and is advanced along the guidewire 84, for example using conventional over-the-guidewire techniques. The tubular body 12 is advanced until the energy delivery section 18 is positioned at the clot 90. In certain embodiments, radiopaque markers (not shown) are optionally positioned along the tubular body energy delivery section 18 to aid in the positioning of the tubular body 12 within the treatment site 88.

As illustrated in FIG. 10C, after the tubular body 12 is delivered to the treatment site 88, the guidewire 84 is withdrawn from the tubular body 12 by pulling the guidewire 84 from the proximal region 14 of the catheter 10 while holding the tubular body 12 stationary. This leaves the tubular body 12 positioned at the treatment site 88.

As illustrated in FIG. 10D, the inner core 34 is then inserted into the tubular body 12 until the ultrasound assembly 42 is positioned at least partially within the energy delivery section 18. In one embodiment, the ultrasound assembly 42 can be configured to be positioned at least partially within the energy delivery section 18 when the inner core 24 abuts the occlusion device at the distal end of the tubular body 12. Once the inner core 34 is positioned in such that the ultrasound assembly 42 is at least partially within the energy delivery section, the ultrasound assembly 42 is activated to deliver ultrasonic energy to the clot 90. As described above, in one embodiment, ultrasonic energy having a frequency between about 20 kHz and about 20 MHz is delivered to the treatment site.

In an example embodiment, the ultrasound assembly 42 includes sixty ultrasound radiating members 40 spaced over a length of approximately 30 to approximately 50 cm. In such embodiments, the catheter 10 can be used to treat an elongate clot 90 without requiring moving or repositioning the catheter 10 during the treatment. However, in modified embodiments, the inner core 34 can be moved or rotated within the tubular body 12 during the treatment. Such movement can be accomplished by maneuvering the proximal hub 37 of the inner core 34 while holding the backend hub 33 stationary.

Figure 11D:
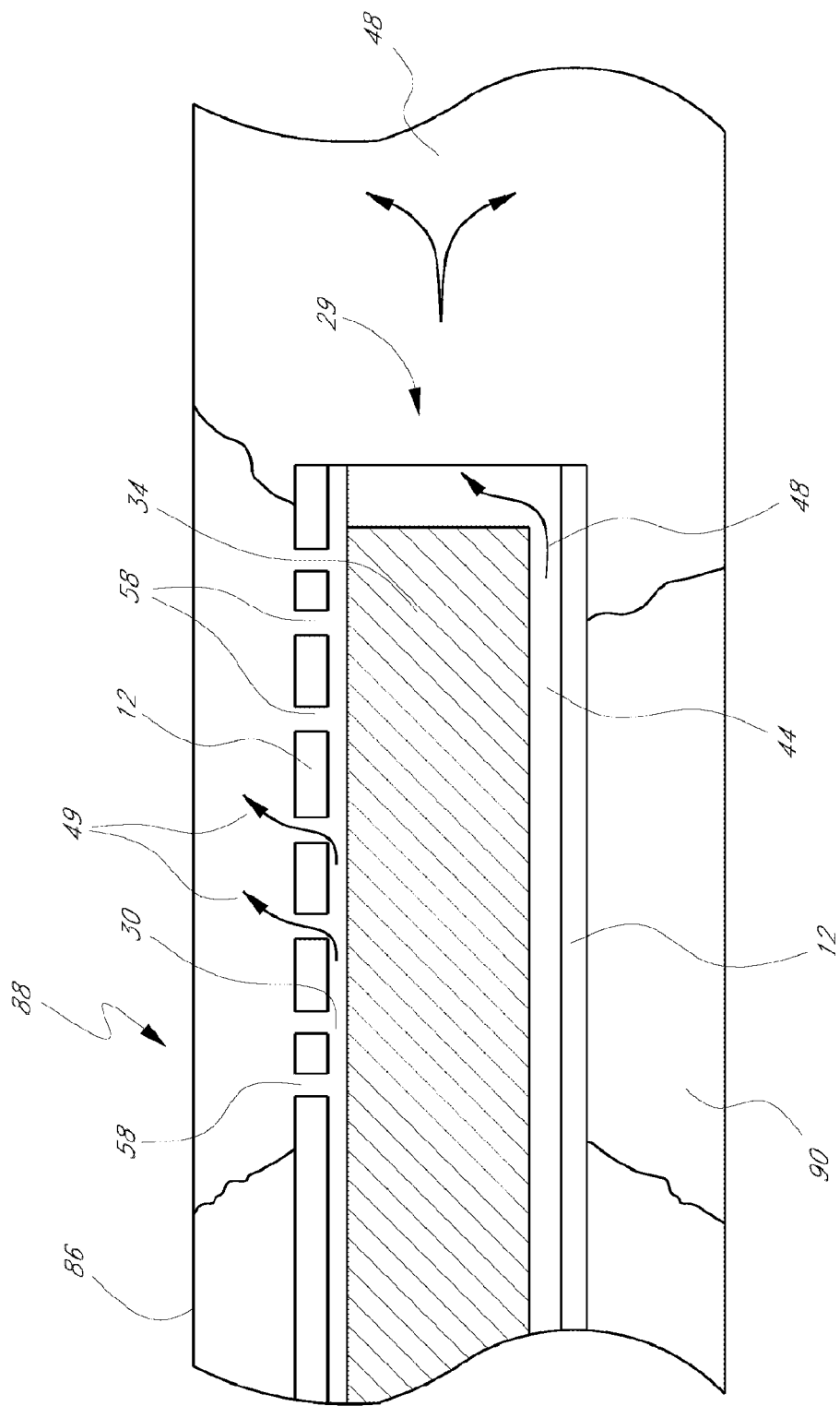
FIG. 11D is a cross-sectional view of the distal end of the ultrasonic catheter of FIG. 11C, wherein an inner core has been inserted into the tubular body to perform a treatment.

Still referring to FIG. 11D, arrows 48 indicate that a cooling fluid can be delivered through the cooling fluid lumen 44 and out the distal exit port 29. Likewise, arrows 49 indicate that a therapeutic compound can be delivered through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Consequently, the methods illustrated in FIGS. 11A through 11D can be performed in a variety of different orders than that described above. In an example embodiment, the therapeutic compound and ultrasonic energy are delivered until the clot 90 is partially or entirely dissolved. Once the clot 90 has been sufficiently dissolved, the tubular body 12 and the inner core 34 are withdrawn from the treatment site 88.

Overview of a Small Vessel Ultrasonic Catheter.

Ultrasonic catheters can also be specifically configured to use in the small vessels of a patient's vasculature, such as in the vasculature of a patient's brain. In such a configuration, the catheter is provided with an energy delivery section having increased flexibility, thereby facilitating delivery of the catheter through narrow vessels having small radius turns. FIGS. 12A and 12B are cross-sectional views of the distal region of an example ultrasonic catheter configured for use in the small vasculature.

Similar to the large vessel ultrasonic catheter described herein, an example ultrasonic catheter configured for use in small vessels comprises a multi-component tubular body 202 having a proximal region and a distal region 206. In such embodiments, the catheter tubular body 202 includes an outer sheath 208 that is positioned upon an inner core 210. In one embodiment, the outer sheath 208 comprises extruded Pebax®, PTFE, polyetheretherketone ("PEEK"), PE, polyamides, braided polyamides and/or other similar materials. The outer sheath distal region 206 is adapted for advancement through vessels having a small diameter, such as those in the vasculature of the brain. In an example embodiment, the outer sheath distal region 206 has an outer diameter between about 2 French and about 5 French. In another embodiment, outer sheath distal region 206 has an outer diameter of about 2.8 French. In one example embodiment, the outer sheath 208 has an axial length of approximately 150 centimeters.

In a modified embodiment, the outer sheath 208 comprises a braided tubing formed of, for example, high or low density polyethylenes, urethanes, nylons, and the like. This configuration enhances the flexibility of the tubular body 202. For enhanced maneuverability, especially the ability to be pushed and rotated, the outer sheath 208 can be formed with a variable stiffness from the proximal to the distal end. To achieve this, a stiffening member may be included along the proximal end of the tubular body 202.

The inner core 210 defines, at least in part, a delivery lumen 212, which, in an example embodiment, extends longitudinally along the catheter. The delivery lumen 212 has a distal exit port 214, and is hydraulically connected to a proximal access port (not shown). Similar to the large vessel ultrasonic catheter described herein, the proximal access port can be connected to a source of therapeutic compound or cooling fluid that is to be delivered through the delivery lumen 212.

In an example embodiment, the delivery lumen 212 is configured to receive a guide wire (not shown). In such embodiments, the guidewire has a diameter of between approximately 0.008 and approximately 0.012 inches. In another embodiment, the guidewire has a diameter of about 0.010 inches. In an example embodiment, the inner core 210 comprises polyamide or a similar material which can optionally be braided to increase the flexibility of the tubular body 202.

Still referring to FIGS. 12A and 12B, the tubular body distal region 206 includes an ultrasound radiating member 224. In such embodiments, the ultrasound radiating member 224 comprises an ultrasound transducer, which converts, for example, electrical energy into ultrasonic energy. In a modified embodiment, the ultrasonic energy can be generated by an ultrasound transducer that is remote from the ultrasound radiating member 224 and the ultrasonic energy can be transmitted via, for example, a wire to the ultrasound radiating member 224.

In the illustrated embodiment, the ultrasound radiating member 224 is configured as a hollow cylinder. As such, the inner core 210 extends through the lumen of the ultrasound radiating member 224. The ultrasound radiating member 224 is secured to the inner core 210 in a suitable manner, such as using an adhesive. A potting material can also be used to further secure the ultrasound radiating member 224 to the inner core 210.

In other embodiments, the ultrasound radiating member 224 can have a different shape. For example, the ultrasound radiating member 224 can take the form of a solid rod, a disk, a solid rectangle or a thin block. In still other embodiments, the ultrasound radiating member 224 can comprise a plurality of smaller ultrasound radiating members. The illustrated configuration advantageously provides enhanced cooling of the ultrasound radiating member 224. For example, in one embodiment, a therapeutic compound can be delivered through the delivery lumen 212. As the therapeutic compound passes through the lumen of the ultrasound radiating member 224, the therapeutic compound can advantageously remove excess heat generated by the ultrasound radiating member 224. In another embodiment, a fluid return path can be formed in the region 238 between the outer sheath 208 and the inner core 21 such that coolant from a coolant system can be directed through the region 238.

In an example embodiment, the ultrasound radiating member 224 produces ultrasonic energy having a frequency of between about 20 kHz and about 20 MHz. In one embodiment, the frequency of the ultrasonic energy is between about 500 kHz and about 20 MHz, and in another embodiment the frequency of the ultrasonic energy is between about 1 MHz and about 3 MHz. In yet another embodiment, the ultrasonic energy has a frequency of about 3 MHz.

In the illustrated embodiment, ultrasonic energy is generated from electrical power supplied to the ultrasound radiating member 224 through a wires 226, 228 that extend through the catheter body 202. The wires 226, 228 cab be secured to the inner core 210, lay along the inner core 210 and/or extend freely in the region 238 between the inner core 210 and the outer sheath 208. In the illustrated configuration, the first wire 226 is connected to the hollow center of the ultrasound radiating member 224, while the second wire 228 is connected to the outer periphery of the ultrasound radiating member 224. In such embodiments, the ultrasound radiating member 224 comprises a transducer formed of a piezoelectric ceramic oscillator or a similar material.

Still referring to the example embodiment illustrated in FIGS. 12A and 12B, the catheter further includes a sleeve 230 that is generally positioned about the ultrasound radiating member 224. The sleeve 230 is comprises a material that readily transmits ultrasonic energy. Suitable materials for the sleeve 230 include, but are not limited to, polyolefins, polyimides, polyester and other materials having a relatively low absorbance of ultrasonic energy. The proximal end of the sleeve 230 can be attached to the outer sheath 208 with an adhesive 232. To improve the bonding of the adhesive 232 to the outer sheath 208, a shoulder 227 or notch can be formed in the outer sheath 208 for attachment of the adhesive 232 thereto. In an example embodiment, the outer sheath 208 and the sleeve 230 have substantially the same outer diameter.

In a similar manner, the distal end of the sleeve 230 can be attached to a tip 234. As illustrated, the tip 234 is also attached to the distal end of the inner core 210. In an example embodiment, the tip 234 is between about 0.5 mm and about 4.0 mm long. In another embodiment, the tip is about 2.0 mm long. In the illustrated example embodiment, the tip 234 is rounded in shape to reduce trauma or damage to tissue along the inner wall of a blood vessel or other body structure during advancement of the catheter to a treatment site.

Referring now to the example embodiment illustrated in FIG. 12B, the catheter includes at least one temperature sensor 236 in the tubular body distal region 206. The temperature sensor 236 can be positioned on or near the ultrasound radiating member 224. Suitable temperature sensors include but are not limited to, diodes, thermistors, thermocouples, RTDs and fiber optic temperature sensors that used thermalchromic liquid crystals. In an example embodiment, the temperature sensor 236 is operatively connected to a control system via a control wire that extends through the tubular body 202. As described above for the large vessel ultrasonic catheter, the control box includes a feedback control system having the ability to monitor and control the power, voltage, current and phase supplied to the ultrasound radiating member 224. Thus, the temperature along the relevant region of the catheter can be monitored and controlled for optimal performance. Details of the control box can also be found in U.S. patent application Ser. No. 10/309,388, filed 3 Dec. 2002, the entire disclosure of which is hereby incorporated herein by reference.

The small vessel ultrasound catheters disclosed herein can be used to remove an occlusion from a small blood vessel. In an example method of use, a guidewire is percutaneously inserted into the patient's vasculature at a suitable insertion site. The guidewire is advanced through the vasculature toward a treatment site where the vessel is wholly or partially occluded. The guidewire is then directed at least partially through the thrombus.

After advancing the guidewire to the treatment site, the catheter is then inserted into the vasculature through the insertion site, and advanced along the guidewire towards the treatment site using, for example, over-the-guidewire techniques. The catheter is advanced until the tubular body distal region 206 is positioned near or in the occlusion. The tubular body distal region 206 optionally includes one or more radiopaque markers to aid in positioning the catheter at the treatment site.

After placing the catheter at the treatment site, the guidewire can then be withdrawn from the delivery lumen 212. A source of therapeutic compound, such as a syringe with a Luer fitting, can then be attached to the proximal access port. This allows the therapeutic compound to be delivered through the delivery lumen 212 and the distal exit port 214 to the occlusion.

The ultrasound radiating member 224 can then be activated to generate ultrasonic energy. As described above, in an example embodiment, the ultrasonic energy has a frequency between about 20 kHz and about 20 MHz. In one embodiment, the frequency of the ultrasonic energy is between about 500 kHz and about 20 MHz, and in another embodiment the frequency of the ultrasonic energy is between about 1 MHz and about 3 MHz. In yet another embodiment, the ultrasonic energy has a frequency of about 3 MHz. The therapeutic compound and ultrasound energy can be applied until the occlusion is partially or entirely dissolved. Once the occlusion has been sufficiently dissolved, the catheter can be withdrawn from the treatment site.

Further information on example methods of use, as well as on modified small vessel catheter constructions, are available in U.S. patent application Ser. No. 10/309,417, filed 3 Dec. 2002, the entire disclosure of which is hereby incorporated herein by reference.

Treatment of Vascular Occlusions Using Ultrasonic Energy and Microbubbles.

In certain embodiments, the therapeutic compound delivered to the treatment site includes a plurality of microbubbles having, for example, a gas formed therein. A therapeutic compound containing microbubbles is referred to herein as a "microbubble compound" or "microbubble therapeutic compound". In an example embodiment, the microbubbles are formed by entrapping microspheres of gas into a therapeutic compound. In one embodiment, this is accomplished by agitating the therapeutic compound while blowing a gas into the therapeutic compound. In another embodiment, this is accomplished by exposing the therapeutic compound to ultrasonic energy with a sonicator under a gaseous atmosphere while vibrating the therapeutic compound. Other techniques for forming the microbubbles are used in other embodiments. Example gases that are usable to form the microbubbles include, but are not limited to, air, oxygen, carbon dioxide, octafluoropropane, and inert gases.

In one embodiment, the microbubble therapeutic compound wholly or partially comprises a suspension of perflutren lipid microspheres, such as that available under the brand name DEFINITY®, which is available from Bristol-Myers Squibb Medical Imaging, Inc. (New York, N.Y.). In such embodiments, the microbubbles comprise octafluoropropane ($C_3F_8$) encapsulated in an outer lipid shell. In one embodiment, the microbubble therapeutic compound is optionally diluted in a phosphate buffered saline solution.

A hemacytometer, microscope and digital camera are usable to view consistent volumes of a microbubble therapeutic compound, thereby enabling quantitative determination of certain properties of the microbubbles in the therapeutic compound. Such properties include quantity of microbubbles per unit volume and microbubble size distribution. In certain applications, such properties are affected by factors such as (a) the temperature at which the microbubble therapeutic compound is stored; (b) the physical handling of the microbubble therapeutic compound by vibrating for a time period or allowing to settle for a time period; (c) the handling of the microbubble therapeutic compound with a syringe; (d) the exposure of the microbubble therapeutic compound to the atmosphere; and (e) the dilution of the microbubble therapeutic compound.

The microbubble therapeutic compound preferably includes between approximately $4 \times 10^6$ and approximately $12 \times 10^9$ microbubbles per milliliter of liquid, more preferably between about $8 \times 10^6$ and about $10 \times 10^9$ microbubbles per milliliter of liquid, and most preferably approximately $4 \times 10^7$ microbubbles per milliliter of liquid. In one embodiment, the quantity of microbubbles per unit volume of carrier fluid is manipulated by diluting the microbubble therapeutic compound in a neutral solution, such as a phosphate buffered saline solution.

The microbubbles preferably have an average diameter that is preferably between approximately 0.01 μm and approximately 100 μm and more preferably between approximately 0.4 μm and approximately 6 μm. The microbubble therapeutic compound is passed through the delivery lumen at a flow rate that is preferably between about 1 mL per hour and about 120 mL per hour, that is more preferably between about 10 mL per hour and about 100 mL per hour, and that is most preferably between about 18 mL per hour and about 22 mL per hour. Optionally, a syringe pump is used to regulate the infusion of microbubble therapeutic compound into the delivery lumen. Other microbubble and delivery parameters are used in other embodiments. For example, in one embodiment pulsed ultrasonic energy having a frequency between about 1 MHz and about 3 MHz (preferably about 1.7 MHz) delivered for between about 15 minutes and about 45 minutes (preferably about 30 minutes) advantageously provides a spatial peak negative pressure of between about 1 MPa and about 2 MPa (preferably between about 1.5 MPa and 2 MPa), which is sufficient to generate therapeutically beneficial cavitation at the treatment site.

In some embodiments, the volume of microbubble therapeutic compound delivered to the catheter treatment zone (also referred to as the "bolus volume") depends on the size of the treatment zone. Table A lists the approximate bolus volume for a treatment zone of a particular size. The values listed in the table are approximate and can be varied at the physician's discretion. For example, in some embodiments, the bolus volume corresponding to a treatment zone of approximately 6 cm is between approximately 0.5 and 2.5 mL; for a treatment zone of approximately 12 cm the bolus volume is between approximately 2 and 4 mL; for a treatment zone of approximately 18 cm the bolus volume is between approximately 3 and 5 mL; for a treatment zone of approximately 24 cm the bolus volume is between approximately 5 and 7 mL; for a treatment zone of approximately 30 cm the bolus volume is between approximately 6 and 8 mL; for a treatment zone of approximately 40 cm the bolus volume is between approximately 8 and 11 mL; and for a treatment zone of approximately 50 cm the bolus volume is between approximately 11 and 13 mL.

TABLE A

| Treatment Zone | Bolus Volume (example) | Bolus Volume (preferred range) |
| --- | --- | --- |
| 6 cm | 1.4 mL | 0.5 mL-2.5 mL |
| 12 cm | 2.9 mL | 2.0 mL-4.0 mL |
| 18 cm | 4.3 mL | 3.0 mL-5.0 mL |
| 24 cm | 5.8 mL | 5.0 mL-7.0 mL |
| 30 cm | 7.2 mL | 6.0 mL-8.0 mL |
| 40 cm | 9.6 mL | 8.0 mL-11.0 mL |
| 50 cm | 12 mL | 11.0 mL-13.0 mL |

Optionally, the fluid in which the microbubbles are suspended does not have therapeutic properties itself, but is merely configured to deliver the microbubbles to the treatment site. Alternatively, the fluid in which the microbubbles are suspended has therapeutic properties, such as a solution containing rtPA that is diluted to a concentration of, for example, between about 2500 IU mL$^{-1}$ and about 7500 IU mL$^{1}$. In other embodiments, some microbubbles can be infused with a drug with therapeutic properties. The drug infused microbubbles may also entrap a gas in addition to the drug. In some embodiments, the entrapped gas itself may be a drug with therapeutic properties, such as nitric oxide. These microbubbles can be delivered to the treatment site and be used to deliver drug to the treatment site when the bubble pops. Drug infused microbubbles can be mixed with non-drug infused microbubbles and be delivered as a mixture. Popping of the drug infused microbubbles, such as through a cavitation process, can be facilitated or enhanced with ultrasound treatment.

In certain configurations, delivering a microbubble therapeutic compound through an optional syringe pump, through a catheter fluid delivery lumen, and past an activated ultrasound radiating member will reduce (a) the concentration of microbubbles delivered to the treatment site, and/or (b) the average size of the microbubbles delivered to the treatment site. Therefore, in an example embodiment the ultrasound radiating member is not activated until all or a portion of the microbubble therapeutic compound is delivered to the treatment site.

In other embodiments, a first portion of the microbubble therapeutic compound is delivered to the treatment site before the ultrasound radiating member is activated, and a second portion of the microbubble therapeutic compound is delivered to the treatment site after the ultrasound radiating member is activated. In still other embodiments, the microbubble therapeutic compound is delivered to the treatment site only when the ultrasound radiating member is active. In embodiments wherein a microbubble therapeutic compound and ultrasonic energy are delivered to the treatment site simultaneously, additional measures are taken to provide a sufficient density of microbubbles at the treatment site. Examples of such additional measures include using a microbubble therapeutic compound with an increased microbubble density, and providing an insulating chamber around the fluid delivery lumen, as described in greater detail below.

In an example embodiment, the efficacy of an ultrasound-based vascular occlusion treatment is enhanced by the presence of microbubbles at the treatment site. In one embodiment, the microbubbles act as a nucleus for cavitation, thus allowing cavitation to be induced at lower levels of ultrasonic energy. Therefore, it is possible to increase the treatment efficacy as a result of cavitation without increasing the amount of ultrasonic energy delivered to the treatment site. In certain embodiments, cavitation also promotes more effective diffusion and penetration of the therapeutic compound into surrounding tissues, such as the clot material. This effect is often referred to as "microstreaming". Furthermore, in some embodiments, the "microjet" mechanical agitation caused by motion of the microbubbles is effective in mechanically breaking up clot material.

While certain vascular treatments are enhanced by the presence of microbubbles at the treatment site, certain intravascular catheter features have an adverse affect on the delivery of a microbubble therapeutic compound to an intravascular treatment site. For example, in certain configurations microbubbles have a tendency to accumulate in and clog the fluid delivery ports 58 and the fluid delivery lumens 30, especially in embodiments wherein a temperature sensor 20 is positioned therein. For example, see the example embodiment illustrated in FIG. 8. This effect is particularly problematic in embodiments wherein the size of the microbubbles are not significantly smaller than the size of the fluid delivery ports 58. For example, as described herein, in certain embodiments the microbubbles have an average diameter of between approximately 0.01 μm and approximately 100 μm, and the fluid delivery ports 58 have an average diameter between about 28 μm and about 48 μm. Additionally, in certain embodiments a portion of the microbubbles are destroyed as a result of the infusion pressure used to deliver the therapeutic compound through the delivery lumens and/the or shear stresses generated by fluid flow through the delivery lumens. The extent to which these structural catheter features affect the concentration of microbubbles that is ultimately delivered to the treatment site depends on several factors, including the flow rate of microbubble therapeutic compound through the delivery lumen and the concentration of the microbubble therapeutic compound delivered through the delivery lumen.

Furthermore, the microbubbles in a microbubble therapeutic compound occasionally cavitate and/or burst when exposed to ultrasonic energy, regardless of whether that exposure occurs inside or outside the fluid delivery lumens of the ultrasonic catheter. When such cavitation occurs within the fluid delivery lumens of the ultrasonic catheter, this not only reduces the quantity of microbubbles delivered to the treatment site, but it also increases the risk of damaging the fluid delivery lumens due to the energy released as a result of the cavitation. The extent to which cavitation occurs within the fluid delivery lumens of an ultrasonic catheter depends on factors such as the flow rate of microbubbles through the lumen (which is proportional to the time the microbubbles are exposed to ultrasonic energy), the concentration of microbubbles in the therapeutic compound (which is proportional to the amount of acoustic shielding for the microbubbles) and the number of active ultrasound radiating members in the catheter (which is proportional to the amount of ultrasonic energy delivered to the lumen). In an example embodiment, the ultrasonic catheter is configured such that the presence of a microbubble therapeutic compound in the delivery lumens does not substantially effect the operation of the ultrasound radiating members.

Therefore, in certain embodiments, the catheter design and/or the treatment techniques are modified to reduce cavitation within the catheter fluid delivery lumens and/or to preserve the quantity of microbubbles delivered to the treatment site. Consequently, in certain embodiments, such modifications advantageously improve the efficacy of a microbubble-based vascular occlusion treatment.

For example, in an embodiment that is particularly advantageous for use with an ultrasonic catheter having a cylindrical ultrasound radiating member (such as that illustrated in FIGS. 12A and 12B) an insulating chamber is used to reduce the amount of ultrasonic energy that is delivered into the catheter fluid delivery lumen. Specifically, an insulating chamber is positioned between the ultrasound radiating member and the delivery lumen. In such embodiments, the insulating chamber is filled with a material that does not efficiently transmit ultrasonic energy, thereby reducing the amount of ultrasonic energy reaching the fluid delivery lumen. Example materials that are put into the insulating chamber include, but are not limited to, air, nitrogen and oxygen. In a modified embodiment, an evacuated chamber is used.

Figure 13:
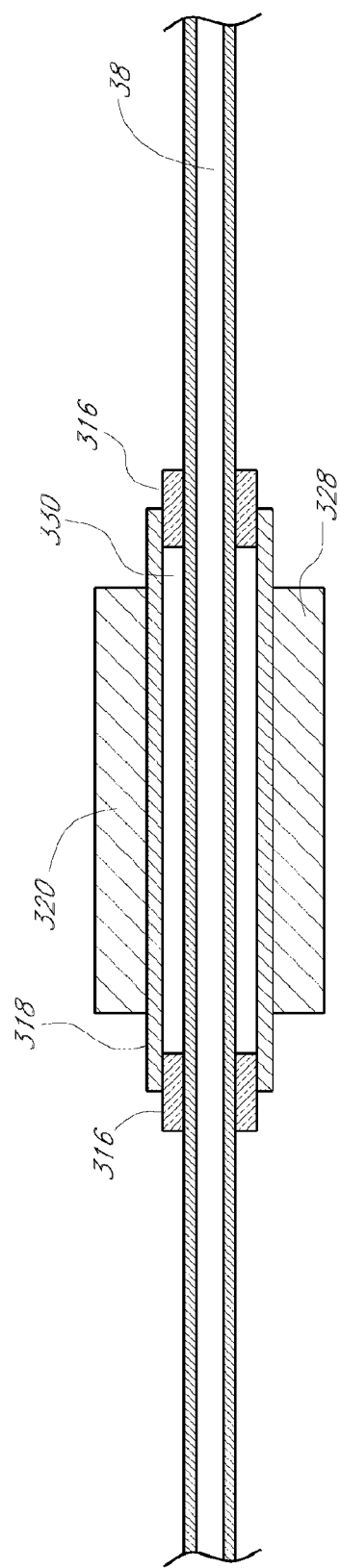
FIG. 13 is a cross-sectional view of an ultrasound radiating member separated from a delivery lumen by a chamber.

FIG. 13 illustrates an example embodiment of an ultrasound catheter having an ultrasound radiating member 320 separated from a delivery lumen 338 by an insulating chamber 330. The ultrasound radiating member 320 is offset from the delivery lumen 338 using spacers 316 and support members 318. Other insulating chamber configurations are used in other embodiments. Additional information on using insulating chambers to spatially direct ultrasonic energy is provided in U.S. Pat. Nos. 6,582,392 and 6,676,626, the entire disclosure of which is incorporated herein by reference.

In another embodiment, a microbubble therapeutic compound is infused intra-arterially or intravenously to the treatment site before the ultrasound radiating members are activated. Therefore, once the ultrasound radiating members begin to generate ultrasonic energy, the microbubble therapeutic compound is already at the treatment site. The microbubble therapeutic compound is delivered using the same catheter that is used to the deliver the ultrasonic energy in some embodiments. The microbubble therapeutic compound is delivered using a different catheter than that used to deliver the ultrasonic energy in other embodiments. The microbubble therapeutic compound is delivered to the treatment site via the general vascular circulation in still other embodiments. Regardless of how the initial delivery of microbubbles to the treatment site is accomplished, ultrasonic energy is delivered to the treatment site after the delivery of microbubbles has occurred. A therapeutic compound or a cooling fluid is optionally delivered to the treatment site during ultrasonic energy delivery, thereby enhancing the treatment efficacy and/or helping to cool the ultrasound radiating members. In one embodiment, a microbubble therapeutic compound is delivered to the treatment site to supplement the concentration of microbubbles provided at the treatment site provided by the initial delivery of microbubbles. Optionally, a cooling element is used to help moderate the temperature of the treatment site.

In a modified embodiment, a microbubble therapeutic compound is delivered to the treatment site intermittently with ultrasonic energy. In one such embodiment, the microbubble therapeutic compound is delivered without ultrasonic energy during a first treatment phase. Subsequently, delivery of the microbubble therapeutic compound is paused and ultrasonic energy is delivered to the treatment site during a second treatment phase. Optionally, the first and second treatment phases are alternately repeated several times. The duration of the first and second phases are each on the order of approximately a few minutes. For example, in one embodiment, the first and second phases each have a duration that is preferably between about 1 minute and about 20 minutes, that is more preferably between about 2 minutes and about 7 minutes, and that is most preferably between about 3 minutes and about 4 minutes. Optionally, the first and second treatment phases have different durations.

Alternating the delivery of microbubble therapeutic compound and ultrasonic energy advantageously reduces the amount of cavitation that occurs within the catheter fluid delivery lumen or lumens. In other embodiments, the therapeutic compound delivered to the treatment site is alternated between a therapeutic compound that contains microbubbles and a therapeutic compound that does not contain microbubbles. In such embodiments, the phases wherein ultrasonic energy is delivered correspond to the phases during in which the therapeutic compound that does not contain microbubbles is delivered.

Figure 14:
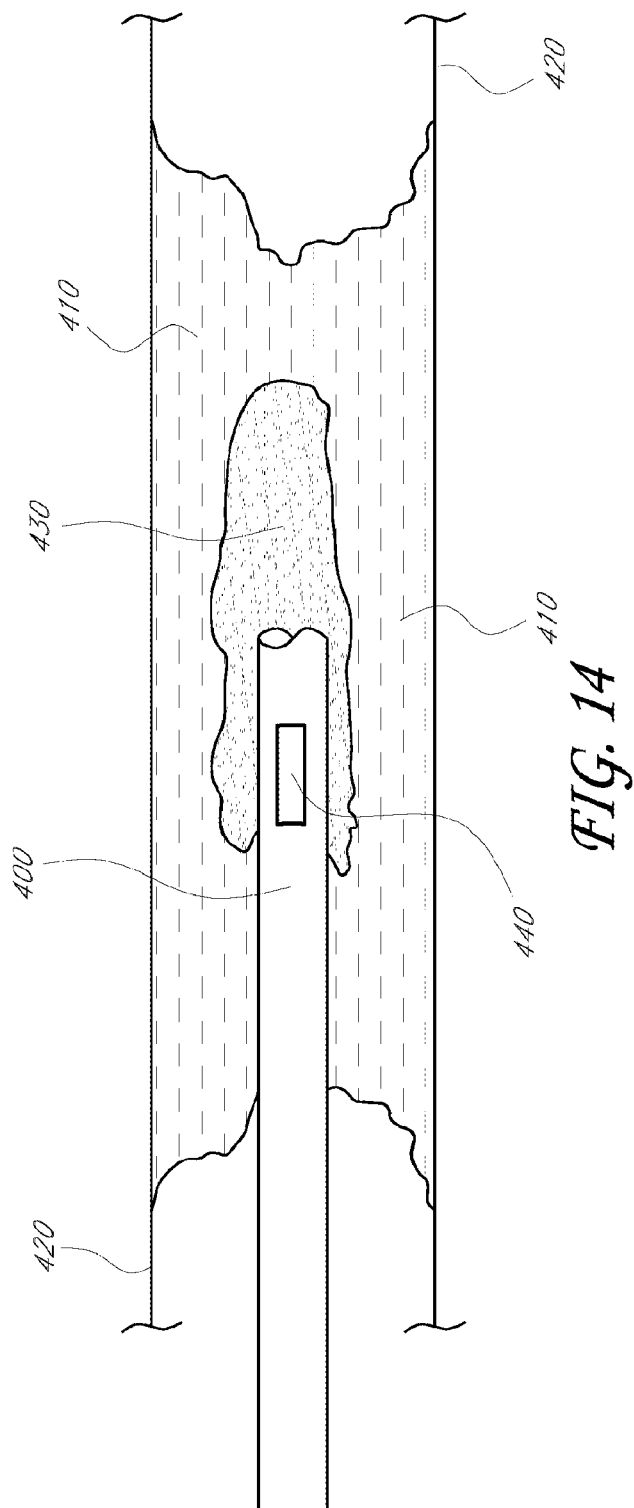
FIG. 14 is a cross-sectional view of an example technique for applying ultrasonic energy to an infused microbubble therapeutic compound.

In one embodiment, the microbubble therapeutic compound is injected directly into a vascular obstruction at the treatment site. A schematic illustration of this embodiment is provided in FIG. 14. Specifically, FIG. 14 illustrates a catheter 400 having a distal end that is positioned within an occlusion 410 in a patient's vasculature 420. A microbubble therapeutic compound 430 has been infused into the occlusion 410 from the catheter 400. Once the microbubble therapeutic compound has been sufficiently infused, one or more ultrasound radiating members 440 mounted within the catheter 400 is energized, thereby delivering ultrasonic energy to the occlusion 410 and the infused microbubble therapeutic compound 430. The catheter 400 is optionally repositioned during the treatment to direct additional ultrasonic energy into a larger portion of the occlusion 410 and the infused microbubble therapeutic compound 430. In such embodiments, ultrasonic energy is applied to the microbubbles suspended within the occlusion, thereby causing mechanical agitation and/or cavitation of the microbubbles. The mechanical agitation and/or cavitation of the microbubbles assists faster enzyme mediated lysis of the clot and/or generates microholes that increase the clot surface area available to interact with lysing enzymes.

As described herein, in certain embodiments control circuitry is used to selectively activate certain ultrasound radiating members in the catheter. In certain embodiments, such control circuitry is also used to selectively activate an infusion pump that controls delivery of a microbubble therapeutic compound through the catheter fluid delivery lumens. Such embodiments advantageously allow the ultrasonic energy and the microbubble therapeutic compound to be separately delivered during distinct periods of the treatment. In an example embodiment, the control circuitry is capable of controlling a wide variety of infusion pump configurations, such as a rotating syringe pump, a peristaltic pump, or another pump that is capable of developing pressure differentials slowly. In a modified embodiment, the pump housing and/or the reservoir from which the microbubble therapeutic compound is drawn in agitated or rotated to prevent settling of the microbubbles during the course of the treatment.

An example system that includes certain of these features is schematically illustrated in FIG. 15. Specifically, FIG. 15 illustrates an intravascular catheter 500 that is capable of receiving a fluid from a first reservoir 502 that contains a microbubble therapeutic compound. The catheter 500 is also capable of receiving an ultrasound control signal from an ultrasound signal generator 504. Controller 506 is configured to control the ultrasound signal generator 504 and an infusion pump 508 that is coupled to the first reservoir 502. The controller 506 is also optionally configured to control an agitator 510 that is capable of vibrating, rotating, or otherwise agitating the first reservoir 502. As described herein, this configuration is advantageously capable of using a single controller 506 to alternatively cause ultrasonic energy and a microbubble therapeutic compound to be delivered from the catheter 500 to the treatment site. The controller 506 is optionally configured to periodically agitate the first reservoir 502 to preserve the concentration of microbubbles in the microbubble therapeutic compound held therein.

In modified embodiments, the intravascular catheter 500 is optionally also capable of receiving a fluid from a second reservoir 512 that contains a therapeutic compound that does not include microbubbles. In such embodiments, the infusion pump 508 is also coupled to the second reservoir, as is configured such that the controller 506 can be used to independently control delivery of fluids from the first reservoir 502 and the second reservoir 512 to the catheter 500. This configuration advantageously allows the controller 506 to be used to alternate delivery of a microbubble therapeutic compound and a therapeutic compound that does not include microbubbles to the catheter 500.

Regardless of the specific delivery techniques, use of a microbubble therapeutic compound provides enhanced clot weight reduction in certain circumstances. For example, in one application a 45±19% clot weight reduction enhancement was provided by supplementing an rtPa-containing therapeutic compound with ultrasonic energy. However, a 88±25% clot reduction enhancement was provided by supplementing an rtPA-containing therapeutic compound with ultrasonic energy and a microbubble-containing solution. As used herein, "clot reduction enhancement" is defined as the clot weight reduction as compared before and after treatment.

Treatment of Vascular Occlusions Using Cavitation Promoting Surface.

Disclosed herein are methods for enhancing the beneficial efect of ultrasonic energy at an intravascular treatment site by promoting cavitation at the treatment site. Aside from manipulating the acoustic parameters of the ultrasonic energy, other techniques for promoting cavitation at the treatment site include supplying an ultrasound contrast agent to the treatment site and/or using an ultrasound catheter that includes a cavitation promoting surface. Use of such techniques reduces the acoustic pressure amplitude required to initiate cavitation, and therefore allows lower levels of ultrasonic energy to be delivered to the treatment site from the ultrasound assembly. This provides several advantages, such as prolonging the life of an ultrasound radiating member and reducing the likelihood of causing thermal damage to the treatment site. While cavitation is used to enhance the delivery and/or effect of a therapeutic compound in certain embodiments, cavitation promotes clot dissolution even in the absence of a therapeutic compound. Indeed, in the context of treating a vascular occlusion, the beneficial effect of cavitation in the absence of a therapeutic compound is often greater than the beneficial effect of a therapeutic compound alone.

Because cavitation promoting surfaces and ultrasound contrast agents are independently capable of inducing cavitation at an intravascular treatment site, in certain embodiments cavitation is induced at an intravascular treatment site using a cavitation promoting surface, but without using an ultrasound contrast agent. Such embodiments advantageously simplify the treatment procedure by eliminating the need to monitor the concentration of the ultrasound contrast agent at the treatment site, reduce the treatment cost, and reduce the risk of systemic complications caused by the ultrasound contrast agent. In other embodiments, cavitation is induced at an intravascular treatment site using a ultrasound contrast agent, but without using a cavitation promoting surface. Such embodiments advantageously are usable with conventional ultrasound catheters that have not been modified to include the cavitation promoting surface. In still other embodiments, both a cavitation promoting surface and an ultrasound contrast agent are used to enhance cavitation at the treatment site. Regardless of whether a ultrasound contrast agent, a cavitation promoting surface, or both, are used to promote cavitation, the generation of free microbubbles at the treatment site is optionally manipulated by adjusting the frequency, peak pressure and duration of ultrasonic energy delivered to the treatment site.

Techniques for using a therapeutic compound that includes microbubbles (that is, a "microbubble therapeutic compound") to enhance the effect of a vascular occlusion treatment have been disclosed herein. In one application a catheter with a cavitation promoting surface is used to deliver a microbubble therapeutic compound to an internal portion of a vascular occlusion, as opposed to the fluid medium surrounding the occlusion. This is particularly important in view of the observation that the viscoelastic properties of the surrounding medium affect how microbubbles respond to ultrasonic energy.

Figure 16A:
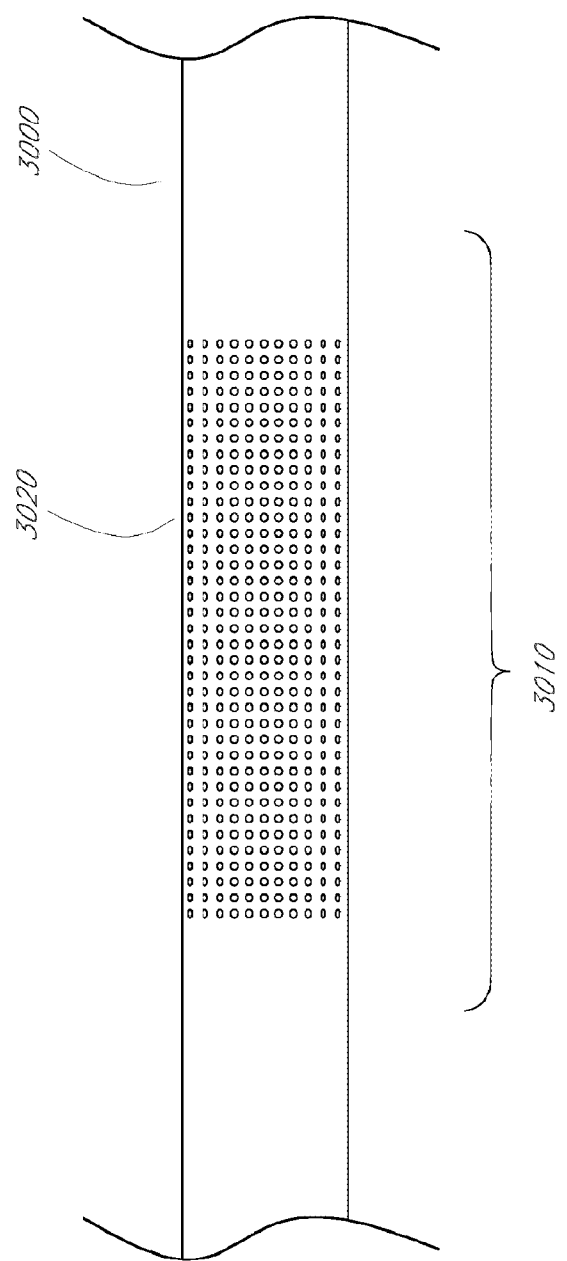
FIG. 16A illustrates a laser patterned cavitation promoting surface.

In some embodiments, a cavitation promoting surface is obtained by patterning a catheter surface with an ablative laser. For example, an excimer laser with mask projection technique can be used to precisely pattern features onto the catheter surface. In some embodiments, the features are holes that are generally circular in shape. In other embodiments, the holes are oval, rectangular, triangular or another geometrical shape. In some embodiments, the features are approximately 15 µm in diameter and/or depth. In other embodiments, the features are between approximately 1 and 100 µm in diameter and/or depth. In some embodiments, the features can be separated by approximately 25 µm. In other embodiments, the features can be separately by a distance between approximately 1 and 100 µm. FIGS. 16A and 16B illustrate an example of a catheter surface 3000 having a laser patterned cavitation promoting surface 3010. As illustrated in FIGS. 16A and 16B, the cavitation promoting surface 3010 comprises holes 3020 that are formed on a portion of the catheter surface 3000. In one embodiment, the holes 3020 do not extend through the catheter body, but instead are formed as surface features on the exterior catheter surface 3000. The cavitation promoting surface 3010 can be formed on the portion of the catheter surface 3000 that is proximate the ultrasound radiating members and/or the energy delivery section of the catheter.

In other embodiments, a cavitation promoting surface is obtained by grit blasting a catheter surface with an angular media. For example, one suitable angular media is a powder of aluminum oxide particles having an average diameter of approximately 25 µm. Aluminum oxide and other similar angular media are dry media, which advantageously facilitate cleaning of the catheter surface after the roughening treatment is performed. In other embodiments, the angular media has a diameter between approximately 1 and 100 µm.

In other embodiments, a cavitation promoting surface is obtained by scoring a catheter surface. In some embodiments, the depth and/or width of the scoring is between approximately 1 and 100 µm. In some embodiments, the scoring is a single continuous spiral that winds around the catheter surface. In other embodiments, the scoring is formed from multiple intersecting spirals that form a cross-hatched pattern on the catheter surface. In other embodiments, the scoring is formed by parallel and non-intersecting scores.

In other embodiments, a cavitation promoting surface is obtained by etching a catheter surface. In some embodiments, the etching is done with chemicals, plasma or laser. An etch mask can be applied to the catheter surface to limit etching to appropriate areas of the catheter surface. In some embodiments, the etching results in features similar to those produced by laser ablation, scoring or grit blasting.

In some embodiments, a hydrophobic coating is applied to the catheter surface either before or after the cavitation promoting surface is formed as described herein. In some embodiments, the hydrophobic coating is formed, for example, from parylene. In some embodiments, application of the hydrophobic coating lowers the surface energy between blood and the cavitation promoting surface allowing for easier bubble liberation.

In other embodiments, a cavitation promoting surface is obtained by coating a catheter surface with a superhydrophobic material with nanoscale porous structures. For example, one such coating material consists of polypropylene with an appropriate solvent, such as p-xylene, and the appropriate nonsolvent, such as methyl ethyl ketone, which is used to precipitate the dissolved polypropylene out of the solvent. After precipitation, the solvent and nonsolvent is removed by evaporation, leaving a film of porous material. In some embodiments, the porous structures provide gas entrapment sites for cavitation nuclei while the superhydrophobic properties reduce the surface energy allowing for easier bubble liberation.

In other embodiments, a cavitation promoting surface is obtained by attaching a porous ceramic, resin, polymer or metal material to a catheter surface. The porous structure acts as a source of entrapped gas for cavitation nuclei.

Treatment of Vascular Occlusions Using Stable and/or Inertial Cavitation.

Although this disclosure is not limited by theory, it is believed that ultrasonic energy accelerates enzymatic fibrinolysis through non-thermal mechanisms by increasing transport of drug molecules into the clot. Mechanical effects of ultrasonic energy such as streaming, radiation force and cavitation have the ability to influence drug transport. Acoustic cavitation is generally acknowledged as playing a significant role in ultrasound-accelerated fibrinolysis. The addition of ultrasound contrast agents has been shown to increase the effectiveness of ultrasound-accelerated enzymatic fibrinolysis. Mechanisms related to both inertial cavitation (for example, intense localized stresses and microjets) and stable cavitation (for example, cavitation microstreaming and bubble translation) are believed to be responsible for the enhanced drug transport and lysis.

In certain embodiments, the type of cavitation activity occurring at the treatment site is determined by analyzing frequency components in the scattered acoustic emissions from the treatment site. For example subharmonic emission at half the driving frequency, which is a characteristic of stable nonlinear bubble oscillation, provides a general indicator for stable cavitation activity. Broadband noise, which is manifested as an elevation in the signal amplitude between the harmonic peaks in the fast Fourier transform ("FFT") magnitude spectrum, provides a general indicator for inertial cavitation activity. In the absence of cavitation, only the fundamental ultrasound drive signal and its harmonics are present, aside from broadband electrical background noise.

In certain embodiments, the broadband noise in a particular signal is quantified by integrating the "inter-peak" noise amplitude NA between 4 and 10 MHz. Other frequency spectra are used in other embodiments. To reference the noise amplitude to a non-cavitating "baseline" signal—such as that obtained in degassed (<36% of saturation), 0.2 µm filtered water—a relative noise enhancement RNE was calculated as the increase in noise amplitude relative to the average baseline noise amplitude <BNA> for n recorded baseline "bursts" of the hydrophone signal:

$$RNE = \left[ \frac{NA - \langle BNA \rangle}{\langle BNA \rangle} \right]$$

A true rise in broadband noise over baseline due to inertial cavitation is identified by setting a detection threshold. For example, in one application the noise enhancement threshold NET is defined as the relative noise enhancement corresponding to 4 times the standard deviation of the baseline noise amplitude SD{BNA} for n recorded baseline bursts:

$$NET = \left[ \frac{4 \times SD\{BNA\}}{\langle BNA \rangle} \right]$$

By searching digitized "snapshots" of noise activity for instances in which the relative noise enhancement crossed the noise enhancement threshold, a total number of ultrasound bursts containing inertial cavitation ("IC count") is determined. Additionally, the maximum relative noise enhancement detected in a snapshot max{RNE} compiled as an average from m independent snapshots is optionally compared between treatments, thereby enabling further statistical analysis.

In certain embodiments, subharmonic emission in a particular signal is identified by the presence of a subharmonic peak in the FFT magnitude spectrum at one half of the fundamental frequency. To quantify the subharmonic content in a recorded burst, the FFT magnitude spectrum is computed and the magnitude at the subharmonic frequency was taken as the subharmonic amplitude SA. To reference the subharmonic amplitude to a non-cavitating baseline signal—such as that obtained in degassed (<36% of saturation), 0.2 μm filtered water—the relative subharmonic enhancement RSE is calculated as the increase in subharmonic amplitude relative to the average baseline subharmonic amplitude <BSA> for n recorded baseline bursts:

$$RSE = \left[ \frac{SA - \langle BSA \rangle}{\langle BSA \rangle} \right]$$

Processed in this way, each digitized burst yields a single measure of the relative subharmonic enhancement, for which it is possible to plot as a function of time over the duration of the snapshot. For a given snapshot, the subharmonic quantities are averaged over the n bursts to yield the average subharmonic enhancement <RSE>. The average value of <RSE> is optionally compiled from m independent snapshots and compared between treatment groups, thereby enabling further statistical analysis.

Figure 17:
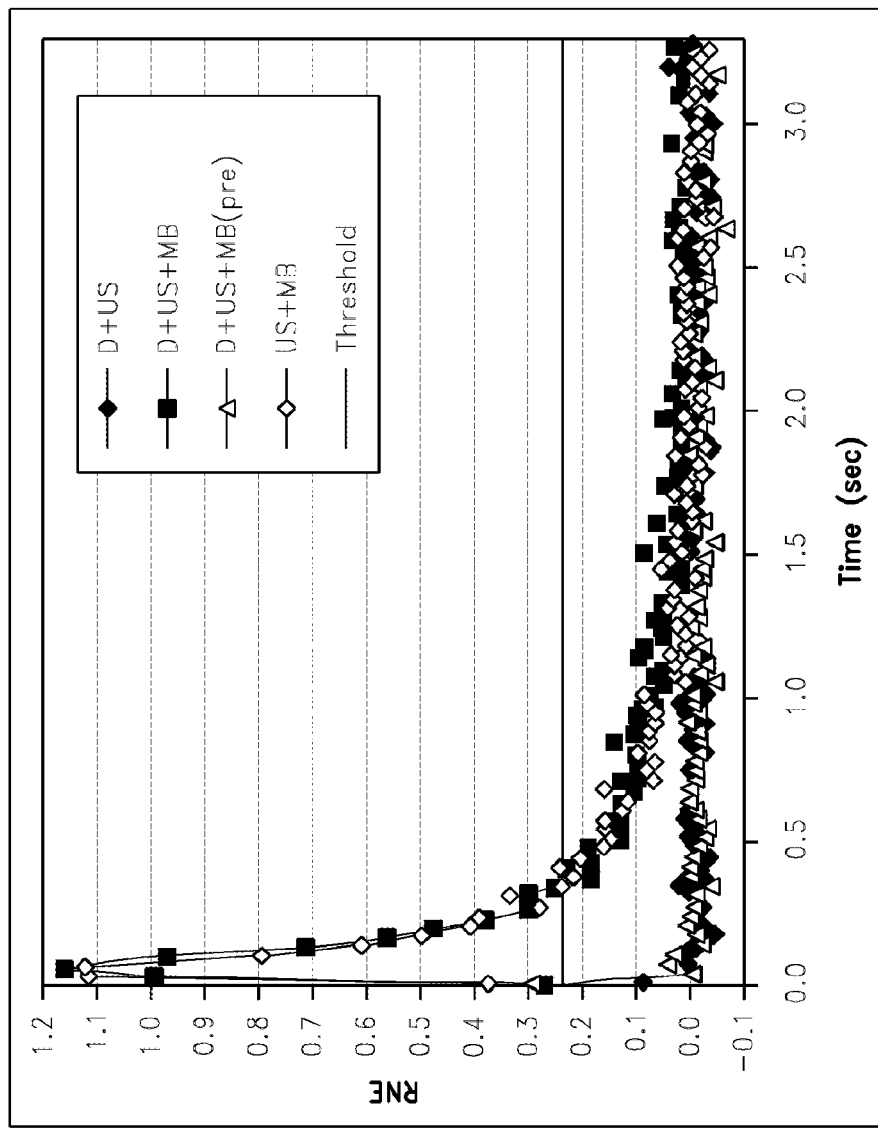
FIG. 17 is a graph showing the relative noise enhancement versus time during a 3.33-second snapshot obtained at time zero in a 30-minute ultrasound exposure. Each trace is an average over 10 snapshots.
Figure 18:
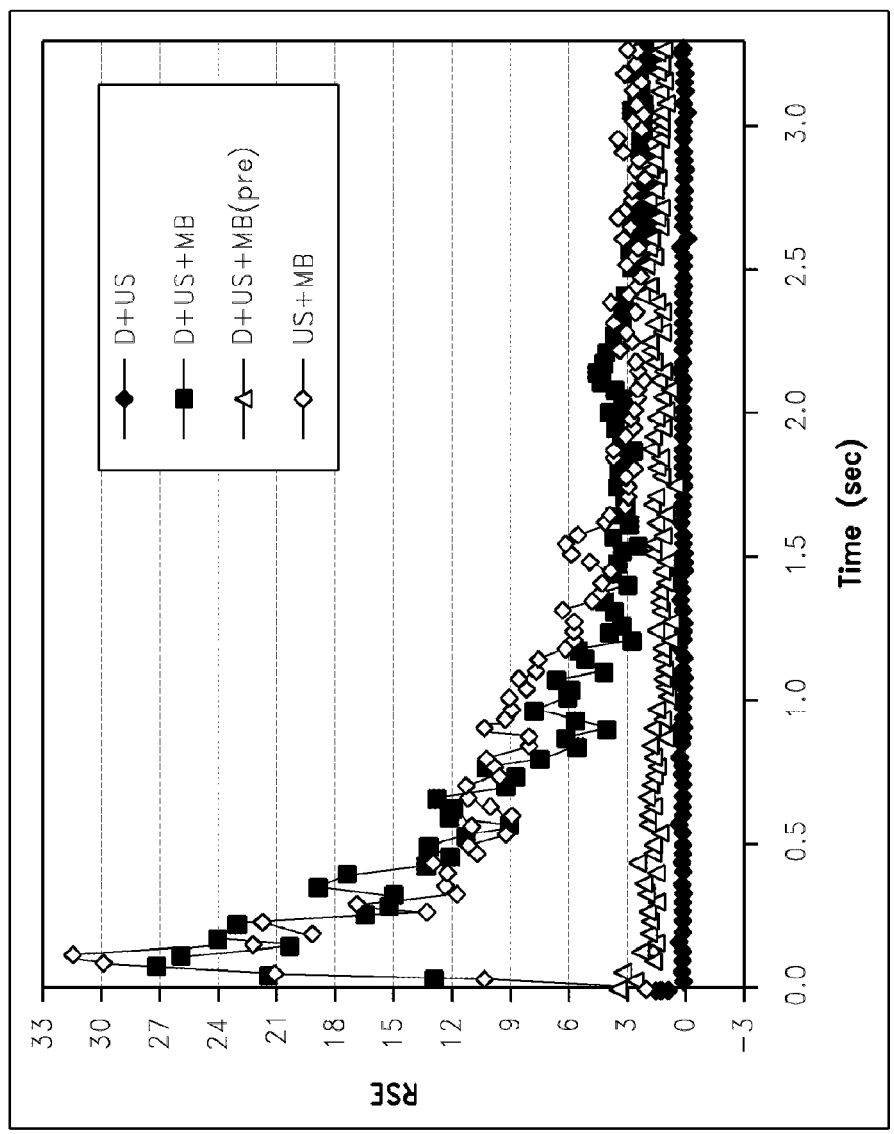
FIG. 18 is a graph showing the relative subharmonic enhancement versus time during a 3.33-second snapshot obtained at time zero in a 30-minute ultrasound exposure. Each trace is an average over 10 snapshots.

A plot illustrating RNE as a function of time during a 3.33-second snapshot for an example 30-minute ultrasound exposure within a clot is illustrated in FIG. 17. A plot illustrating RSE as a function of time during a 3.33-second snapshot for an example ultrasound exposure within a clot is illustrated in FIG. 18. Data from four treatment protocols are illustrated in FIGS. 17 and 18: therapeutic compound and ultrasonic energy (D+US); therapeutic compound, ultrasonic energy, and microbubbles (D+US+MB); therapeutic compound, ultrasonic energy, and microbubbles that were previously exposed to ultrasound (D+US+MB(pre)); and ultrasonic energy and microbubbles (US+MB).

As illustrated in FIGS. 17 and 18, in the absence of microbubbles (D+US), both RNE and RSE remained at baseline. When microbubbles were present, cavitation signals were high and were substantially identical for the two protocols in which the microbubbles were not pre-exposed to ultrasonic energy (D+US+MB and US+MB). RNE increased rapidly to a peak value within about 0.1 seconds, decreased toward baseline, crossed below the detection threshold (NET≈0.24) at about 0.4 seconds, and settled to baseline by about 1.0 seconds. Similarly, RSE increased to a peak value within about 0.1 seconds. However, RSE did not settle back to baseline, but instead remained at a slightly elevated value during the remainder of the snapshot. For the protocol in which microbubbles were pre-exposed to ultrasonic energy (D+US+MB(pre)), broadband noise and subharmonic activity were reduced compared to the other microbubble-based protocols. Specifically, elevation in RNE was observed in generally the first ultrasound burst, which immediately dropped to baseline by the next burst. On the other hand, RSE remained at a low, steady amplitude slightly above baseline.

Figures 19A, 19B:
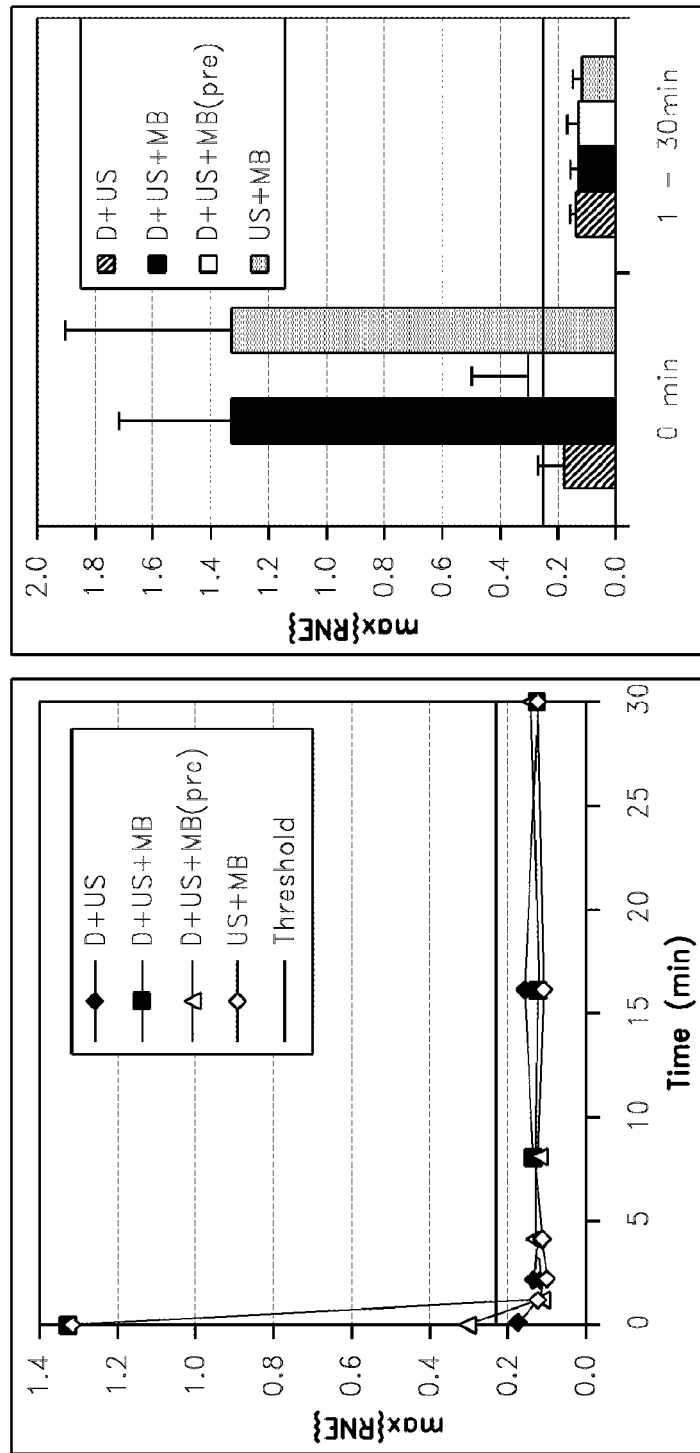
FIG. 19A is a graph showing the maximum noise enhancement per snapshot illustrated as a function of ultrasound exposure time. Each point corresponds to an average of 10 snapshots.
FIG. 19B is a graph showing a comparison of max{RNE} for the snapshot taken at time zero (0 min) and the average max{RNE} for snapshots obtained during the remainder of the 30-minute exposure. Error bars indicate standard deviation.
Figures 20A, 20B:
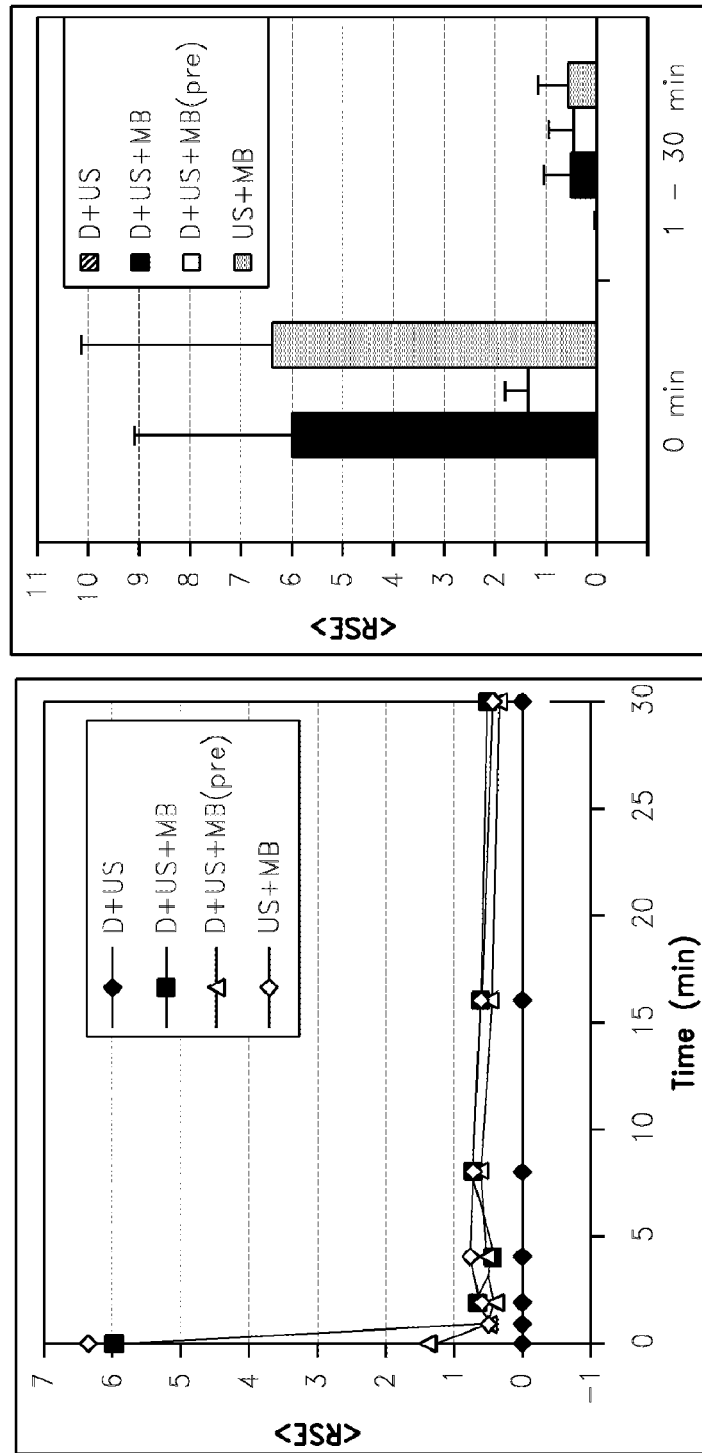
FIG. 20A is a graph showing the average subharmonic enhancement per snapshot illustrated as a function of ultrasound exposure time. Each point corresponds to an average of 10 snapshots.
FIG. 20B is a graph showing a comparison of <RSE> for the snapshot taken at time zero and the average <RSE> for snapshots obtained during the remainder of the 30-minute exposure. Error bars indicate standard deviation.

The cavitation signal quantities per snapshot measured at various times throughout the 30-minute exposure are shown in FIGS. 19A and 19B (max{RNE}) and FIGS. 20A and 20B (<RSE>). In the absence of microbubbles (D+US), max{RNE} remained below the detection threshold for the entire 30-minute exposure, and <RSE> remained at baseline. For the snapshot taken at time zero, max{RNE} for each of the microbubble-based protocols was significantly greater than that for the non-microbubble (D+US) protocol (p<0.033). The max{RNE} for both the (D+US+MB) and the (US+MB) protocols were significantly greater than that for the (D+US+MB(pre)) protocol (p<0.001). For the remainder of the 30-minute exposure, max{RNE} for the microbubble-based protocols showed no significant difference from the non-microbubble (D+US) protocol. For all microbubble-based protocols <RSE> was significantly greater than that for the non-microbubble (D+US) protocol during both the snapshot at time zero (p<0.001) and during the remainder of the 30-minute exposure (p<0.010).

Table B lists the total number of IC counts observed for the different treatment protocols. In accordance with the max{RNE} trends shown in FIGS. 19A and 19B, IC counts were only observed during the initial snapshot in the 30-minute exposure. The number of counts was greatest for the two protocols in which microbubbles were not pre-exposed to ultrasound (D+US+MB and US+MB). In the absence of microbubbles (D+US), two IC counts were recorded.

TABLE B

| | Time Window | D + US | D + US + MB | D + US + MB (pre) | US + MB |
|---|---|---|---|---|---|
| Total Number of Bursts Analyzed | 0 min | 1000 | 1000 | 1000 | 1000 |
| | 1-30 min | 6000 | 6000 | 6000 | 6000 |
| Total Number of IC Counts | 0 min | 2 | 103 | 5 | 111 |
| | 1-30 min | 0 | 0 | 0 | 0 |

In the absence of microbubbles, pulsed ultrasonic energy significantly accelerates rtPA-induced fibrinolysis in certain applications. In such applications, thermal mechanisms are not believed to have played a role in lysis enhancement. The minimal degree of heating observed is considered to be insufficient to account for the increased lysis. Cavitation signals were either not detected (subharmonic amplitude remained at baseline) or were negligible (only two IC counts) in the corresponding radiated acoustic signal, suggesting that the observed lysis enhancement in the absence of microbubbles was due to non-cavitation mechanical effects of the ultrasonic energy.

In embodiments wherein microbubbles are dispersed within the clot, lysis enhancement due to ultrasonic energy increased significantly, confirming the synergistic effect of microbubbles and therapeutic compound. Inertial cavitation, observed as broadband noise in the acoustic signal, was present only at the start of the ultrasound exposure, and disappeared completely in less than one second. Subharmonic emission, an indicator for stable cavitation activity, was greatest at the start of the exposure, subsequently decreased in amplitude, yet persisted for the remainder of the 30-minute treatment. Without being limited by theory, the limited duration of inertial cavitation is explained by liberated microbubbles yielding sub-resonant bubbles (for example, bubbles smaller than resonance size at 1.7 MHz) that break up upon collapse, thereby forming very small bubbles that are quickly driven to dissolution by the compressive force of surface tension.

In the presence of microbubbles alone, ultrasound exposure resulted in no measurable lysis, indicating that mechanical disruption (for example, fragmentation) of the clot was not a contributing mechanism for lysis. This lack of effect is not surprising because of the limited duration of inertial cavitation observed. Optionally, the microbubbles are replenished, or the acoustic parameters (such as acoustic pressure amplitude, pulse length, or duty cycle) are modified to increase the persistence and quantity of inertial cavitation to an extent where mechanical effects alone become important.

In embodiments wherein microbubbles were pre-exposed to ultrasound prior to therapeutic compound delivery, the cavitation activity that occurred at the start of the treatment was significantly reduced compared to the other microbubble-based protocols. In particular, inertial cavitation was substantially eliminated: only the first ultrasound burst contained broadband noise. Without being limited by theory, a possible explanation for this result is that all of the candidate sub-resonant bubbles were "used up" in the pre-exposure and thus were not available to nucleate inertial cavitation when the therapeutic compound was present. The low-amplitude subharmonic emission, however, was still present during the 30-minute exposure and at the same magnitude as in the other protocols with microbubbles. Without being limited by theory, this result suggests the presence of super-resonant bubbles. Super-resonant bubbles are large bubbles that are less influenced by surface tension, that do not dissolve as quickly as smaller bubble, and that are held in place by the dense fibrin matrix of the clot. Lysis enhancement in such embodiments was substantially the same as that obtained for treatments in which microbubbles were not pre-exposed to ultrasound.

Without being limited by theory, these results suggest that the increased lysis enhancement in the presence of microbubbles was correlated with the subharmonic emission that occurred throughout the 30-minute treatment, and that the brief inertial cavitation that occurred at the beginning of the exposure was inconsequential. This suggests that mechanisms related to stable cavitation (for example, steady micro-streaming) rather than inertial cavitation (for example, mechanical disruption and transient micro-jets) were responsible for the increased lysis in the presence of microbubbles. In embodiments wherein sustained inertial cavitation is achieved using modified acoustic parameters, it is possible to obtain an even greater degree of lysis enhancement.

In certain embodiments the additional lysis enhancement due to microbubbles is correlated to the presence of the subharmonic emission, thus identifying an important role for stable cavitation in microbubble-enhanced ultrasound-accelerated fibrinolysis. Mechanisms related to stable cavitation, such as steady micro-streaming, enhance fibrinolysis by promoting local mass transfer and thus the rate of penetration of the therapeutic compound into the clot matrix. Thus, in certain embodiments inertial cavitation is optionally reduced or eliminated without adversely effecting the enhancement of ultrasound-accelerated fibrinolysis in the presence of microbubbles. Thus, in such embodiments it is possible to avoid the safety risks associated with inertial cavitation (for example, tissue hemorrhage and hemolysis) while still enjoying the lysis-enhancing effect of microbubbles by choosing ultrasound exposure parameters to promote stable cavitation while minimizing or eliminating inertial cavitation.

As described herein, subharmonic emission was used as a general indicator for stable cavitation. In certain embodiments, other types of stable bubble activity, including oscillations that occur below the pressure threshold for subharmonic emission, occur simultaneously and are also responsible for lysis enhancement. However, surface waves on the bubble wall, which have been associated with subharmonic emissions, are effective in generating micro-streaming flows around bubbles undergoing repetitive large amplitude motion.

SCOPE OF THE INVENTION

While the foregoing detailed description discloses several embodiments of the present invention, it should be understood that this disclosure is illustrative only and is not limiting of the present invention. It should be appreciated that the specific configurations and operations disclosed can differ from those described above, and that the methods described herein can be used in contexts other than treatment of vascular occlusions.

We claim:
1. A system for treating an occlusion within a patient's vasculature with ultrasonic energy, the system comprising:
   a catheter configured to be passed through the patient's vasculature such that a portion of the catheter is positioned at an intravascular treatment site, wherein the catheter includes a fluid delivery lumen having a distal fluid delivery port;
   an ultrasound radiating member positioned within the catheter;
   an ultrasound signal generator configured to supply a drive signal to the ultrasound radiating member so as to cause ultrasonic energy to be delivered to the treatment site;
   an infusion pump configured to pump a therapeutic compound into the fluid delivery lumen so as to cause the therapeutic compound to be delivered through the distal fluid delivery port to the treatment site;
   a first reservoir configured to hold the therapeutic compound;

an agitator configured to supply mechanical vibrations to the first reservoir, wherein the agitator and the ultrasound signal generator are separate elements; and a controller configured to control the ultrasound signal generator and the infusion pump such that (a) when the ultrasound signal generator is supplying the drive signal to the ultrasound radiating member the infusion pump is in an idle state, and (b) when the infusion pump is pumping a therapeutic compound into the fluid delivery lumen the ultrasound signal generator is in an idle state.

2. The system of claim 1, wherein the infusion pump is selected from the group consisting of a rotating syringe pump and a peristaltic pump.

3. The system of claim 1, wherein the therapeutic compound is a microbubble therapeutic compound.

4. The system of claim 3, wherein the microbubble therapeutic compound has a microbubble concentration between approximately $4 \times 10^6$ and approximately $12 \times 10^9$ microbubbles per milliliter.

5. The system of claim 3, wherein the microbubble therapeutic compound has an average microbubble diameter that is between approximately 0.4 µm and approximately 6 µm.

6. The system of claim 3, wherein the microbubble therapeutic compound comprises octafluoropropane encapsulated in a plurality of lipid shells.

7. The system of claim 1, wherein the infusion pump is configured to pump the therapeutic compound into the delivery lumen at an infusion rate that is between approximately 10 mL per hour and approximately 120 mL per hour.

8. The system of claim 1, wherein:
the therapeutic compound is a microbubble therapeutic compound; and
the infusion pump is configured to pump the therapeutic compound from the first reservoir into the fluid delivery lumen.

9. The system of claim 8, further comprising a second reservoir configured to hold a supplemental therapeutic compound, wherein the infusion pump is further configured to pump the supplemental therapeutic compound from the second reservoir into the fluid delivery lumen.

10. The system of claim 9, wherein the supplemental therapeutic compound does not include microbubbles.

11. The system of claim 10, wherein the controller is further configured to control the infusion pump such that when the ultrasound signal generator is supplying the drive signal to the ultrasound radiating member the infusion pump is not pumping the therapeutic compound into the fluid delivery lumen, and is pumping the supplemental therapeutic compound into the fluid delivery lumen.

12. The system of claim 1, wherein the controller is configured to control the agitator.

13. The system of claim 1, wherein the distal fluid delivery port is positioned adjacent to the ultrasound radiating member, such that a therapeutic compound delivered from the distal fluid delivery port is within an ultrasonic energy field generated by the ultrasound radiating member.

14. The system of claim 1, wherein the catheter further comprises a plurality of surface features formed on an exterior surface of a body of the catheter, wherein the plurality of holes do not extend through the body of the catheter.

15. The system of claim 14, wherein the plurality of surface features are holes.

16. The system of claim 15, wherein the plurality of holes have a diameter between approximately 1 and 100 µm.

17. The system of claim 14, wherein the plurality of surface features are located in a distal region of the body of the catheter.

18. The system of claim 14, wherein the plurality of surface features are hydraulically isolated from the fluid delivery lumen.

19. A system comprising:
a catheter having a proximal region and a distal region, the catheter including (a) a fluid delivery lumen extending from an infusion port in the proximal region to a delivery port in the distal region, (b) an ultrasound radiating member positioned in the distal region, and (c) an elongate conductor extending from the ultrasound radiating member to the proximal region;

an ultrasound signal generator configured to supply a drive signal to the ultrasound radiating member via the elongate conductor;

a microbubble therapeutic compound reservoir coupled to the infusion port via an infusion pump, the infusion pump being configured to pump fluid from the microbubble therapeutic compound reservoir into the infusion port;

an agitator configured to impart mechanical motion to the microbubble therapeutic compound reservoir, wherein the agitator and the ultrasound signal generator are separate elements; and a controller configured to control the ultrasound signal generator and the infusion pump such that (a) when the infusion pump is pumping fluid into the infusion port the ultrasound signal generator is not supplying a drive signal to the ultrasound radiating member, and (b) when the infusion pump is not pumping fluid into the infusion port the ultrasound signal generator is supplying a drive signal to the ultrasound radiating member.

20. The system of claim 19, wherein the catheter includes a plurality of ultrasound radiating members positioned in the distal region.

21. The system of claim 19, wherein the ultrasound radiating member is movable relative to the delivery port.

22. The system of claim 19, wherein the ultrasound radiating member is a hollow cylinder, and wherein the fluid delivery lumen passes through the ultrasound radiating member.

23. The system of claim 19, wherein the controller is further configured to control the agitator.

24. The system of claim 19, further comprising a therapeutic compound reservoir coupled to the infusion port via the infusion pump.

25. The system of claim 24, wherein the controller is configured to control the infusion pump such that the infusion pump does not pump fluid into the infusion port from the microbubble therapeutic compound reservoir and the therapeutic compound reservoir simultaneously.

26. The system of claim 25, wherein the controller is further configured to pump fluid into the infusion port from the therapeutic compound reservoir when the ultrasound signal generator is supplying a drive signal to the ultrasound radiating member.

* * * * *